United States Patent
Trieu

(10) Patent No.: US 10,053,504 B2
(45) Date of Patent: Aug. 21, 2018

(54) SPARC BINDING SCFVS

(71) Applicant: Abraxis BioScience, LLC, Los Angeles, CA (US)

(72) Inventor: Vuong Trieu, Agoura Hills, CA (US)

(73) Assignee: ABRAXIS BIOSCIENCE, LLC, Los Angeles, CA (US)

( * ) Notice: Subject to any disclaimer, the term of this patent is extended or adjusted under 35 U.S.C. 154(b) by 0 days.

(21) Appl. No.: 15/132,647

(22) Filed: Apr. 19, 2016

(65) Prior Publication Data

US 2016/0304592 A1 Oct. 20, 2016

Related U.S. Application Data

(62) Division of application No. 14/451,858, filed on Aug. 5, 2014, now Pat. No. 9,314,537, which is a division of application No. 13/132,455, filed as application No. PCT/US2009/067032 on Dec. 7, 2009, now Pat. No. 8,809,507.

(60) Provisional application No. 61/120,228, filed on Dec. 5, 2008.

(51) Int. Cl.
| | |
|---|---|
| *A61K 39/00* | (2006.01) |
| *C07K 16/18* | (2006.01) |
| *C07K 14/51* | (2006.01) |
| *A61K 39/44* | (2006.01) |
| *A61K 49/00* | (2006.01) |
| *C12N 9/96* | (2006.01) |
| *G01N 33/53* | (2006.01) |
| *C07K 14/78* | (2006.01) |
| *C07K 14/705* | (2006.01) |
| *A61K 47/68* | (2017.01) |
| *A61K 39/395* | (2006.01) |
| *A61K 38/00* | (2006.01) |

(52) U.S. Cl.
CPC .......... *C07K 16/18* (2013.01); *A61K 39/3955* (2013.01); *A61K 39/44* (2013.01); *A61K 47/6835* (2017.08); *A61K 47/6851* (2017.08); *A61K 49/0002* (2013.01); *A61K 49/0056* (2013.01); *C07K 14/51* (2013.01); *C07K 14/70521* (2013.01); *C07K 14/78* (2013.01); *C12N 9/96* (2013.01); *G01N 33/53* (2013.01); *A61K 38/00* (2013.01); *A61K 39/395* (2013.01); *A61K 39/39558* (2013.01); *A61K 2039/505* (2013.01); *C07K 2317/52* (2013.01); *C07K 2317/622* (2013.01); *C07K 2317/70* (2013.01); *C07K 2317/732* (2013.01); *C07K 2317/734* (2013.01); *C07K 2319/00* (2013.01); *C07K 2319/30* (2013.01)

(58) Field of Classification Search
CPC .................. A61K 2039/505; A61K 39/39558
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,569,789 A | 2/1986 | Blattler et al. | |
| 4,642,334 A | 2/1987 | Moore et al. | |
| 4,816,567 A | 3/1989 | Cabilly et al. | |
| 4,952,394 A | 8/1990 | Senter | |
| 5,137,877 A | 8/1992 | Kaneko et al. | |
| 5,349,066 A | 9/1994 | Kaneko et al. | |
| 5,500,362 A | 3/1996 | Robinson et al. | |
| 5,612,474 A | 3/1997 | Patel | |
| 5,618,528 A | 4/1997 | Cooper et al. | |
| 5,821,337 A | 10/1998 | Carter et al. | |
| 6,696,245 B2 | 2/2004 | Winter et al. | |
| 7,332,568 B2 | 2/2008 | Trieu et al. | |
| 8,415,304 B2 | 4/2013 | Trieu et al. | |
| 8,420,603 B2 | 4/2013 | Trieu et al. | |
| 9,295,733 B2 * | 3/2016 | Trieu ................ | C07K 14/51 |
| 2006/0015952 A1 | 1/2006 | Filvaroff | |
| 2006/0115476 A1 | 6/2006 | Tedesco et al. | |
| 2006/0204529 A1 | 9/2006 | Keiichi | |
| 2007/0054271 A1 | 3/2007 | Polyak et al. | |
| 2007/0117133 A1 | 5/2007 | Trieu et al. | |
| 2007/0154901 A1 | 7/2007 | Thogersen | |
| 2008/0255035 A1 | 10/2008 | Trieu et al. | |

FOREIGN PATENT DOCUMENTS

| | | |
|---|---|---|
| CN | 1980699 A | 6/2007 |
| CN | 101160321 A | 4/2008 |
| EP | 1440981 A2 | 7/2004 |
| JP | 2001-520397 A | 10/2001 |
| JP | 2002-521053 A | 7/2002 |
| JP | 2007-537460 A | 12/2007 |
| WO | WO 00/73430 A2 | 12/2000 |
| WO | WO 2005/117952 A2 | 12/2005 |

(Continued)

OTHER PUBLICATIONS

Bergers et al. (Current Opinion in Genetics and Development. 2000; 10: 120-127).*
Kelland (Eur. J. Cancer. Apr. 2004; 40 (6): 827-836).*
Saijo et al. (Cancer Sci. Oct. 2004; 95 (10): 772-776).*
Dennis (Nature. Aug. 7, 2006; 442: 739-741).*
Gura (Science. 1997; 278: 1041-1042).*
McDevitt et al. (Cancer Res. Nov. 1, 2000; 60: 6095-6100).*
Henry et al. (Cancer Res. Nov. 1, 2004; 64: 7995-8001).*
Takeshita et al. (Leukemia. Jul. 2009; 23 (7): 1329-36).*
Bernard et al. (Human Immunol. 1986; 17: 388-405).*
Pettersen et al. (J. Immunol. Jun. 15, 1999; 162 (12): 7031-7040).*
Abass et al. (eds.), *Cellular and Molecular Immunology*, p. 54, Philadelphia, W.B. Saunders (1991).
Berg et al., *Biochem. J.*, 307, 313-326 (1995).

(Continued)

*Primary Examiner* — Stephen Rawlings
(74) *Attorney, Agent, or Firm* — Leydig, Voit & Mayer, Ltd.

(57) ABSTRACT

The invention provides compositions comprising SPARC binding ScFv and its use.

4 Claims, 20 Drawing Sheets

(56) References Cited

FOREIGN PATENT DOCUMENTS

| WO | WO 2006/079120 A2 | 7/2006 |
|---|---|---|
| WO | WO 2008/060651 A2 | 5/2008 |
| WO | WO 2008/128169 A1 | 10/2008 |
| WO | WO 2008/143708 A2 | 11/2008 |

OTHER PUBLICATIONS

Boder et al., *PNAS*, 97(20), 10701-10705 (Sep. 26, 2000).
Bradford, Marion M., *Analytical Biochem.*, 72, 248-254 (1976).
Caldas et al., *Mol Immunol.*, 39(15), 941-952 (May 2003).
Carlsson et al., *Biochem. J.*, 173, 723-737 (1978).
Carmen et al., *Briefings in Functional Genomics and Proteornics*, 1 (2), 189-203 (Jul. 2002).
Casset et al., *Biochem Biophys Res Commun.*, 307(1), 198-205 (Jul. 18, 2003).
Chien et al., *Proc Natl Acad Sci USA*, 86(14), 5532-5536 (Jul. 1989).
Clonis, Yarinis D., *J. Chromatography A*, 1101, 1-24 (2006).
Clynes et al., *Proc. Natl. Acad. Sci. USA*, 95, 652-656 (Jan. 1998).
Cumber et al., *Bioconjugate Chem.*, 3, 397-401 (1992).
Daugherty et al., *Protein Engineering*, 11(9), 825-832 (1998).
De Pascalis et al., *J Immunol.*, 169(6), 3076-3084 (Sep. 15, 2002).
Endo et al., *Curr. Opn., Biotech.*, 17, 373-380 (2006).
Fattom et al., *Infection and Immun.*, 60(2), 584-589 (Feb. 1992).
Fuglsang. Anders, *Protein Exp. Purif.*, 31, 247-249 (2003).
Genbank Accession No. CAF32930.1 (Mar. 3, 2004).
Georgiou et al., *Curr. Opn. Biotech.*, 7, 190-197 (1996).
Goldmacher et al., *Bioconjugate Chem.*, 3 104-107 (1992).
Gordon, *Proc. Natl. Acad. Sci. USA*, 84, 308-312 (Jan. 1987).
Greenwald et al., *Adv. Drug Del. Rev.*, 55, 217-250 (2003).
Giusti et al., *Proc Natl Acad Sci USA*, 84(9), 2926-2930 (May 1987).
Gussow et al., *Methods Enzymol.*, 203, 99-121 (1991).
Hazum et al., "A Photocleavable Protecting Group for the Thiol Function of Cysteine," *Proceedings of the 16th European Peptide Symposium*, Helsingør, Denmark (1980).
Holm et al., *Mol Immunol.*, 44(6), 1075-1084 (Feb. 2007).
Hooper et al., *Biochem. J.*, 321, 265-279 (1997).
Jayaraj et al., *Nuc. Acids Res.*, 33(9), 3011-3016 (2005).
Jmeian et al., *Electrophoresis*, 30, 249-261 (2009).
Kelm et al., *Blood*, 75(5), 1105-1113 (Mar. 1, 1990).
Koukourakis et al., *Cancer Res.*, 63, 5376-5380 (Sep. 1, 2003).
Kozak, Marilyn, *J. Mol. Biol.*, 196, 947-950 (1987).
Lane et al., *FASEB J.*, 8, 163-173 (1994).
Lowry et al., *J. Biol. Chem.*, 193, 265-275 (1951).
MacCallum et al., *J Mol Biol.*, 262(5), 732-745 (Oct. 11, 1996).
Mahan et al., *Anal. Biochem.*, 162, 163-170 (1987).
Malaval et al., *J. Bone and Mineral Res.*, 6(4), 315-323 (1991).
Mao et al., *Proc. Natl. Acad. Sci, USA*, 96, 6953-6958 (Jun. 1999).
Mariuzza et al., *Annu Rev Biophys Biophys Chem.*, 16, 139-159 (1987).
Murakami et al., *Biochem. Biophys. Res. Comm.*, 146(3), 1249-1255 (Aug, 14, 1987).
Needleman et al., *J. Mol. Biol.*, 48, 443-453 (1970).
Parikh et al., *BioTechniques*, 24, 428-431 (Mar. 1998).
Queen et al., *Proc. Natl. Acad. Sci. USA*, 86, 10029-10033 (Dec. 1989).
Roitt, Ivan et al., *Immunology*, $5^{th}$ ed., pp. 110-113 and 150-153, Mosby (2000).
Rudikoff et al., *Proc. Natl. Acad. Sci., USA*, 79, 1979-1983 (Mar. 1982).
Sambrook et al., *Molecular Cloning: A Laboratory Manual*, Third Ed., pp. 1.1-1.162, Cold Spring Harbor Laboratory Press, Cold Spring Harbor, NY (2001).
Sambrook et al., *Molecular Cloning: A Laboratory Manual*, Third Ed., pp. 15.1-15.53, Cold Spring Harbor Laboratory Press, Cold Spring Harbor, NY (2001).
Sambrook et al., *Molecular Cloning: A Laboratory Manual*, Third Ed., pp. 16.1-16.54, Cold Spring Harbor Laboratory Press, Cold Spring Harbor, NY (2001).
Schechter et al., *Biochem. Biophys. Res. Comm.*, 27(2), 157-162 (1967).
Senter et al., *Photochem. and Photobiol.*, 42(3), 231-237 (1985).
Seo et al., *App. Environ. Microbiol.*, 73 (17), 5598-5606 (Sep. 2007).
Singer et al., *Genes and Genornes*, vol. 1, p. 63. Moscow, Mir (1998).
Singh et al., *Bioinformatics*, 17 (12) 1236-1237 (2001).
Smith et al., *Anal. Biochem.*, 150(1),76-85 (Oct. 1985).
Smyth et al., *Immunol. Today*, 16(4), 202-206 (1995).
Sorensen et al., *J. Biotech.*, 115, 113-128 (2005).
Sweetwyne et al., *J. Histochem & Cytochem.*, 52(6), 723-733 (2004).
Talanian et al., *J. Biol. Chem.*, 272(15), 9677-9682 (Apr. 11, 1997).
Thornberry et al., *J. Biol. Chem.*, 272(29), 17907-17911 (Jul. 18, 1997).
Thorpe et al., *Cancer Res.*, 47, 5924-5931 (Nov. 15, 1987).
Vajdos et al., *J Mol Biol.*, 320(2), 415-428 (Jul. 5, 2002).
Walden et al., *J. Mol. Cell Immunol.*, 2, 191-197 (1986).
Wawrzynczak et al., *Br. J. Cancer*, 66(2), 361-366 (1992).
Wellhöner et al., *J. Biol. Chem.*, 266(7), 4309-4314 (1991).
Werb, Zena, *Cell*, 91, 439-442 (Nov. 14, 1997).
Winkler et al., *J Immunol.*, 165(8), 4505-4514 (Oct. 15, 2000).
Wolfsberg et al., *J. Cell Biol.*, 131(2), 275-278 (Oct. 1995).
Wu et al., "The Synthetic Gene Designer: a Flexible Web Platform to Explore Sequence Space of Synthetic Genes for Heterologous Expression," *Proceedings, IEEE Computational Systems Bioinformatics Conference Workshops* (2005).
Yen et al., *Makromol. Chem.*, 190, 69-82 (1989).
Fandy et al., *Mol. Cancer*, 7, 60 (2008).
Jalota-Badhwar et al., *J Biol. Chem.*, 282(13), 9902-9913 (Mar. 30, 2007).
Kessler et al., *Clin. Cancer Res.*, 11(17), 6317-6324 (Sep. 1, 2005).
Kondo et al., *Exp. Cell Res.*, 264, 117-125 (2001).
Mocellin et al., *Cytokine & Growth Factor Reviews*, 16, 35-53 (2005).
Smyth et al., *Immunity*, 18, 1-6 (Jan. 2003).

\* cited by examiner

FIG. 3

| SEQ. ID NO | Sequence | Count |
|---|---|---|
|  | Total | 134 |
| 3 | AHPWRYTEPWSW | 6 |
| 4 | ALSRHHHPIFPR | 4 |
| 5 | NEVVPFSYARQS | 3 |
| 6 | HVPHLASIMASN | 2 |
| 7 | HWGLHLSAWSQM | 2 |
| 8 | HWKPWTSPSRHS | 2 |
| 9 | IDKPLHVVLALG | 2 |
| 10 | SPCAYTSTCDAL | 2 |
| 11 | SYSYPNLKSAYN | 2 |
| 12 | THHPTFYLTRAP | 2 |
| 13 | TPHQNPWFFEIT | 2 |
| 14 | TQWHDDSTFYWL | 2 |
| 15 | TVNTYYNYGMSP | 2 |
| 16 | TWHASAPRPPLL | 2 |
| 2 | VTPLLKFRALSS-21 | 2 |
| 18 | AAAPLNLSMTFP | 1 |
| 19 | AALTFFAPQSAS | 1 |
| 20 | ALVPKNLTPPQH | 1 |
| 21 | ANWSPWHHYHHK | 1 |
| 22 | APAHPHTAYPSG | 1 |
| 23 | ATWHSFFYHNHS | 1 |
| 24 | AYSHSTPSSLTE | 1 |
| 25 | DDNNLFWWNNAQ | 1 |
| 26 | DGMFNYRASLDP | 1 |
| 27 | DLHGRTSSTPPD | 1 |
| 28 | DPLQPPDNVTYF | 1 |
| 29 | DQAASRSHSFPL | 1 |
| 30 | EHGSALFRWSQT | 1 |
| 31 | EVFHWTAGTPRE | 1 |
| 32 | THSSESRRMSPT | 1 |
| 33 | FQSVPSKNIATH | 1 |
| 34 | GHHHPSATFNAR | 1 |
| 35 | GHSASFALHSSD | 1 |
| 36 | GLTSVKHHHNAH | 1 |
| 37 | GMDFRTLIWPHK | 1 |
| 38 | GMHVPQIPGHFL | 1 |
| 39 | GTIGPFPETLRL | 1 |
| 40 | HGPHDMTIVGMG | 1 |
| 41 | HHLFQIHPDSWP | 1 |
| 42 | HHYKTDLHRTPR | 1 |
| 43 | HLKHLNWTASKL | 1 |
| 44 | HLPKSLS | 1 |
| 45 | HMKSQTDTPFYG | 1 |
| 46 | HQMELIGTGHWG | 1 |
| 47 | HTLHHMTTSPFA | 1 |
| 48 | HTNLMQTTRPLV | 1 |
| 49 | HVHQHRHLVEVI | 1 |
| 50 | HWLPLLGGFLSA | 1 |
| 51 | HYFSRTQTLSTL | 1 |
| 52 | HYQFHWRSLSGP | 1 |
| 53 | IHRAPTPFNLGT | 1 |
| 54 | HPLRMNTAYPY | 1 |
| 55 | IPFATAAYNAPG | 1 |
| 56 | KAYLDSIPITPR | 1 |
| 57 | KVTTNYALHLAS | 1 |
| 58 | LPFPLSYNIGPA | 1 |
| 59 | LPPPPHLPTFLP | 1 |
| 60 | LPTFNFSLPGI | 1 |
| 61 | LSTHKLFHSHSQ | 1 |
| 62 | MDTPGHLHLSRS | 1 |
| 63 | MKEAPIDGSCL | 1 |
| 64 | NFAQNLSSNTYW | 1 |
| 65 | NGYLGLRPQLHF | 1 |
| 66 | NHLNSMSSVEAL | 1 |
| 67 | NHQLHQPIHFPRM | 1 |
| 68 | NLTHPLWGPDLF | 1 |
| 69 | NTLSQPRVGGLN | 1 |
| 70 | NTPPMSHQNPVR | 1 |
| 71 | QDALTPRRLWPT | 1 |
| 72 | QILGYPTNLGPF | 1 |
| 73 | QYDTHRGSDNKQ | 1 |
| 74 | RHLEINHVTLLV | 1 |
| 75 | SAHTLAAWFAKP | 1 |
| 76 | SETLQVYKPILY | 1 |
| 77 | SHLILSSPSRGV | 1 |
| 78 | SIHSTQDRFVHPA | 1 |
| 79 | SIHYPTARQLTMS | 1 |
| 80 | SIAPHSQRLSLS | 1 |
| 81 | SILPDISTRGLAA | 1 |
| 82 | SIPPHPARYYSPL | 1 |
| 83 | SIPPTTMTPNNMP | 1 |
| 84 | SSHPIPYNASQM | 1 |
| 85 | STYKDSWNEYGP | 1 |
| 86 | SYQQPMGLYRQF | 1 |
| 87 | TGLLQEPTFRGM | 1 |
| 88 | THGHYYPSIALS | 1 |
| 89 | TLPAAALPWLYL | 1 |
| 90 | TMIPLIYPPQAN | 1 |
| 91 | TPDLSQSSPHSF | 1 |
| 92 | TPHLPPTRAGSP | 1 |
| 93 | TPNPLGTQCMTC | 1 |
| 94 | TQYIHTDLSSTS | 1 |
| 95 | TSHQIYPVSWMR | 1 |
| 96 | TSSASHTNLTTR | 1 |
| 97 | TSTRQIWSTHDL | 1 |
| 98 | TSYLNSGMIPAR | 1 |
| 99 | TTHSELSGYVEL | 1 |
| 100 | VEAENDSGMNSQ | 1 |
| 101 | VFDLNGYNRNPI | 1 |
| 102 | VGNMPFVHPHQW | 1 |
| 103 | VPATRVSPTPYA | 1 |
| 104 | VSHPPRFPGWPQ | 1 |
| 105 | WHEPSTWLVNPR | 1 |
| 106 | WPAHPHTAYPSG | 1 |
| 107 | WPINQQRQLYTS | 1 |
| 108 | WSDPRAVTWRAP | 1 |
| 109 | WSLTPTALLTSF | 1 |
| 110 | WSVPLPPGDPKP | 1 |
| 111 | YMAPHVPLTNAS | 1 |
| 112 | YPNPWHESSFMS | 1 |
| 121 | YSAHIGSRHTHY | 1 |
| 1 | YTRLHHWIPPQR-15 | 1 |

FIG. 4

| Clone | OD | | | Sequences | SEQ ID NO: |
|---|---|---|---|---|---|
| 15 | 0.597 | 0.516 | 0.576 | YTRLHHWIPPQR | 1 |
| 21 | 0.450 | 0.443 | 0.438 | VTPLLKFRALSS | 2 |
| 59 | 0.737 | 0.628 | 0.733 | VSHPPRFPGWPQ | 104 |
| 60 | 0.619 | 0.611 | 0.605 | KAYLDSIPITPR | 56 |
| 63 | 0.686 | 0.664 | 0.602 | TSYLNSGMIPAR | 98 |
| 101 | 0.592 | 0.551 | 0.607 | AHPWRYTEPWSW | 3 |
| 133 | 0.545 | 0.554 | 0.5 | VPATRVSPTPYA | 103 |
| 135 | 0.626 | 0.652 | 0.66 | QILGYPTNLGPF | 72 |
| 154 | 0.612 | 0.665 | 0.674 | AHPWRYTEPWSW | 3 |
| 180 | 1.211 | 1.281 | 1.135 | LSTHKLFHSHSQ | 61 |
| 182 | 0.756 | 0.782 | 0.643 | AAAPLNLSMTFP | 18 |
| 184 | 0.634 | 0.635 | 0.554 | IDKPLHVVLALG | 9 |
| 186 | 0.903 | 0.985 | 0.882 | TQWHDDSTFYWL | 14 |
| 188 | 0.716 | 0.682 | 0.685 | TTHSELSGYVEL | 99 |
| 191 | 0.564 | 0.567 | 0.58 | IPFATAAYNAPG | 55 |
| 192 | 0.567 | 0.5 | 0.539 | VGNMPFVHPHQW | 102 |
| 194 | 0.494 | 0.514 | 0.521 | HYFSRTQTLSTL | 51 |
| 204 | 0.8 | 0.748 | 0.779 | SAHTLAAWFAKP | 75 |

YTRLHHWIPPQR (#15) – SEQ ID NO: 1
VTPLLKFRALSS (#21) – SEQ ID NO: 2

```
tacccgcc tgcatcattg gattccgccg cagcgcgaca aaactcacac atgcccaccg tgcccagcac ctgaactcct ggg    SEQ ID NO: 122
    y  t  r  l  h  h     v  i  p  p     q  r  d     k  t  h     c  p  p     c  p  a     p  e  l     l      SEQ ID NO: 123
>>................15................>>
                            >>................Human IgG1 Fc................>>
```

PD21

```
gtgaccccgc tgctgaaatt tcgcgcgctg agcagcgaca aaactcacac atgcccaccg tgcccagcac ctgaactcct ggg    SEQ ID NO: 124
    v  t  p     l  l  k     f  r  a  l     s  s  d     k  t  h     c  p  p     c  p  a     p  e  l     l      SEQ ID NO: 125
>>................21................>>
                            >>................Human IgG1 Fc................>>
```

PD15 = 4.1 ÷ 0.8 X $10^{-7}$ M . N = 3
PD21 = 1.0 ÷ 0.7 X $10^{-9}$ M . N = 3
mAb = 6.2 ÷ 3.4 X $10^{-8}$ M . N = 3

FIG. 12

Site 2 of Elastin

```
        QGGCQSPAPSCSWAWCWHPWTWSWCRRPWTWSWCWCSWTWSWCWCSWLRGST
SEQ ID NO:117
```

FIG. 15

ScFv 3-1 = SEQ NO: 113

Sequence 1 (Clone 5)
Amino Acid Sequence:

AIRMTQSPSSLSASVGDRVTITC<u>QASQDISNYLN</u>WYQQKPGKAPKLLIY<u>DASNLET</u>GVPSRFSGSGSGTDFTLTI
　　　　　　　　　　　　　　　　L1　　　　　　　　　　　　　　　　　L2

←Heavy　　　　　　　　　Light→
SSLQPEDFATYYC<u>QQSYSTPYT</u>FGQGTKLDIKR|SGGSTITSYNVYYTKLSSSGT|EVQLVQSGAEVKKPGSSVKVS　　ScFv 3-1
　　　　　　　L3

CKASGGTFS<u>SYAIS</u>WVRQAPGQGLEWMG<u>GIIPIFGTANYAQKFQG</u>RVTITADESTSTAYMELSSLRSEDTAVYYC
　　　　　　H1　　　　　　　　　　　H2

AR<u>DPEDNWGAFDI</u>WGQGTMVTVSSAS
　　　H3

Sequence 2 (Clone 17)
Amino Acid Sequence:

EIVMTQSPGTLSLSPGDRATLSC<u>RASQSVSGYLA</u>WYQQKPGQAPRLLIY<u>DASNRAT</u>GIPARFSGSGSGTDFTLTI
　　　　　　　　　　　　　　　　L1　　　　　　　　　　　　　　　　　L2

←Heavy　　　　　　　　　Light→
SSLQAEDVAVYYC<u>QQYYSTLPT</u>FGQGTKLEIKR|SGGSTITSYNVYYTKLSSSGT|QVQLVQSGGGVVQPGRPLKLS　　ScFv 3-2
　　　　　　　L3

CAASGFTFS<u>SYAMH</u>WVRQAPGKGLEWVA<u>VISYDGSNKYYADSVKG</u>RFTISRDNSKNTLYLQMNSLRAEDTAVYYC
　　　　　　H1　　　　　　　　　　　H2

AR<u>DLSWNDAEDI</u>WGQGTMVTVSSAS
　　　H3

ScFv 3-2 = SEQ NO: 114

FIG. 16

ScFv 2-1 = SEQ NO: 115

Sequence 1 (Clone 25)
Amino Acid Sequence:

EVQLLESGGGLVQPGGSLRLSCAASGFTFS SYAMS WVRQAPGKGLEWVS MITPLGSTTAYADSVKG RFTISRDNSK
                              H1                    H2

← Heavy         | Light →
NTLYLQMNSLRAEDTAVYYCAK RAGVFDY WGQGTLVTVSS GGGGSGGGGSGGGGS T DIQMTQSPSSLSASVGDRVTI    ScFv 2-1
                       H3

TC RASQSISSYLN WYQQKPGKAPKLLIY RASTLQS GVPSRFSGSGSGTDFTLTISSLQPEDFATYYC QQNDSFPT
   L1                          L2                                      L3

T FGQGTKVEIKR

Sequence 2 (Clone 16)
Amino Acid Sequence:

EVQLLESGGGLVQPGGSLRLSCAASGFTFS SYAMS WVRQAPGKGLEWVS HIQGQGRATYYADSVKG RFTISRDNSK
                               H1                   H2

← Heavy         | Light →
NTLYLQMNSLRAEDTAVYYCAK THGKFDY WGQGTLVTVSS GGGGSGGGGSGGGGS T DIQMTQSPSSLSASVGDRVT     ScFv 2-2
                       H3

ITC RASQSISSYLN WYQQKPGKAPKLLIY RASRLQS GVPSRFSGSGSGTDFTLTISSLQPEDFATYYC QQPSGVPT
    L1                          L2                                      L3

T FGQGTKVEIK

ScFv 2-2 = SEQ NO: 116

FIG. 17

SCFV 3.1 (SEQ ID NO: 113)

AIRMTQSPSSLSASVGDRVTITCQASQDISNYLNWYQQKPGKAPKLLIYDASNLETGVPSRFSGSGSGTDFTLTISSLQPEDFATYYCQQ
SYSTPYTFGQGTKLDIKRSGGSTITSYNVYYTKLSSSGTEVQLVQSGAEVKKPGSSVKVSCKASGGTFSSYAISWVRQAPGQGLEWMG
GIIPIFGTANYAQKFQGRVTITADESTSTAYMELSSLRSEDTAVYYCARDPEDNWGAFDIWGQGTMVTVSSAS

SCFV 3.2 (SEQ ID NO: 114)

EIVMTQSPGTLSLSPGDRATLSCRASQSVSGYLAWYQQKPGQAPRLLIYDASNRATGPARFSGSGSGTDFTLTISSLQAEDVAVYYCQ
QYYSTLPTFGQGTKLEIKRSGGSTIISYNVYYTKLSSSGTQVLVQSGGVVQPGRPLKLSCAASGFTFSSYAMHWVRQAPGKGLEW
VAVISYDGSNKYYADSVKGRFTISRDNSKNTLYLQMNSLRAEDTAVYYCARDLSWNDAFDIWGQGTMVTVSSAS

SCFV 2.1 (SEQ ID NO: 115)

EVQLLESGGGLVQPGGSLRLSCAASGFTFSSYAMSWVRQAPGKGLEWVSMITPLGSTTAYADSVKGRFTISRDNSKNTLYLQMNSLR
AEDTAVYYCAKRAGVFDYWGQGTLVTVSSGGGGSGGGGSGGGGSTDIQMTQSPSSLSASVGDRVTITCRASQSISSYLNWYQQKPG
KAPKLLIYRASTLQSGVPSRFSGSGSGTDFTLTISSLQPEDFATYYCQQNDSFPTTFGQGTKVEIKR

SCFV 2.2 (SEQ ID NO: 116)

EVQLLESGGGLVQPGGSLRLSCAASGFTFSSYAMSWVRQAPGKGLEWVSHIQGGRATYYADSVKGRFTISRDNSKNTLYLQMNSL
RAEDTAVYYCAKTHGKFDYWGQGTLVTVSSGGGGSGGGGSGGGGSTDIQMTQSPSSLSASVGDRVTITCRASQSISSYLNWYQQKP
GKAPKLLIYRASRLQSGVPSRFSGSGSGTDFTLTISSLQPEDFATYYCQQPSGVPITFGQGTKVEIK

FIG. 18

Purification of scFv 2.1 from bacteria

A.

scFv 2.1 in pBAD

MKKLLFAIPLVVPFYSHSTMEEVQLLESGGGLVQPGGSLRLSCAASGFTFSSYAMSWVRQ
APGKGLEWVSMITPLGSTTAYADSVKGRFTISRDNSKNTLYLQMNSLRAEDTAVYYCAKR
AGVFDYWGQGTLVTVSSGGGGSGGGGSGGGGSTDIQMTQSPSSLSASVGDRVTITCRASQ
SISSYLNWYQQKPGKAPKLLIYRASTLQSGVPSRFSGSGSGTDFTLTISSLQPEDFATYY
CQQNDSFPTTFGQGTKVEIKRFLEQKLISEEDLNSAVDHHHHHH
(SEQ ID NO: 126)

B.

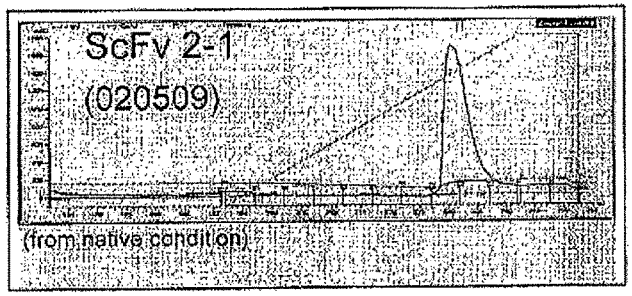

C.

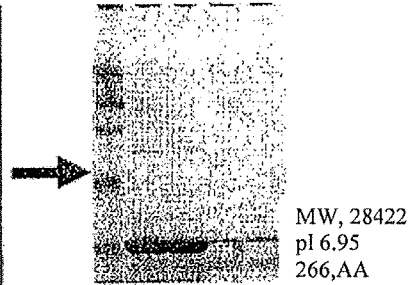

MW, 28422
pI 6.95
266,AA

D.

| Cycle Number | Amino Acid |
|---|---|
| 1 | T |
| 2 | M |
| 3 | E |
| 4 | E |
| 5 | V |

FIG. 19

Purification of scFv 3.1 from bacteria

A.

scFv 3.1 in pBAD

<u>MKKLLFAIPLVVPFYSHSTME</u>AIRMTQSPSSLSASVGDRVTITCQASQDISNYLNWYQQK
PGKAPKLLIYDASNLETGVPSRFSGSGSGTDFTLTISSLQPEDFATYYCQQSYSTPYTFG
QGTKLDIKRSGGSTITSYNVYYTKLSSSGTEVQLVQSGAEVKKPGSSVKVSCKASGGTFS
SYAISWVRQAPGQGLEWMGGIIPIFGTANYAQKFQGRVTITADESTSTAYMELSSLRSED
TAVYYCARDPEDNWGAFDIWGQGTMVTVSSASRSFLEQKLISEEDLNSAVDHHHHHH
(SEQ ID NO: 127)

B. 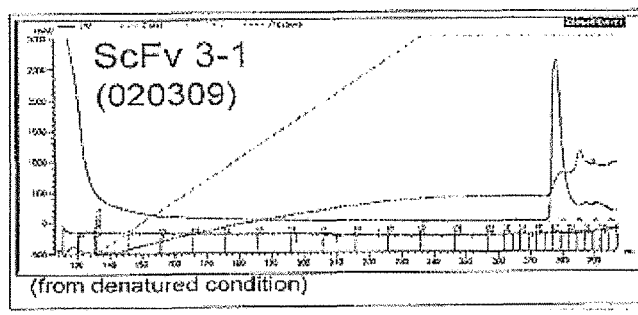 C. 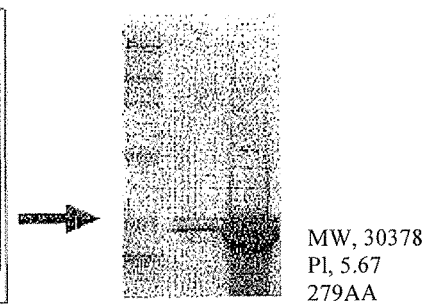

MW, 30378
PI, 5.67
279AA

D.

| Cycle Number | Amino Acid | | |
|---|---|---|---|
| 1 | T | M | |
| 2 | M | K | |
| 3 | D | V | |
| 4 | A | Q | L |
| 5 | I | K | L |

Kinetics of binding with SPARC

| kD (M) | scFv 2.1(S) | scFv 3.1(S) | scFv 3.2 (R) |
|---|---|---|---|
| HTI SPARC | $3.3 \times 10^{-7}$ | $4.4 \times 10^{-6}$ | $7.8 \times 10^{-5}$ |
| Abx SPARC | $3.7 \times 10^{-7}$ | $6.3 \times 10^{-6}$ | $1.3 \times 10^{-6}$ |

S, soluble; R, Refolded, Abx = abraxis

```
                         SEQUENCE LISTING

<160> NUMBER OF SEQ ID NOS: 146

<210> SEQ ID NO 1
<211> LENGTH: 12
<212> TYPE: PRT
<213> ORGANISM: Artificial
<220> FEATURE:
<223> OTHER INFORMATION: Synthetic

<400> SEQUENCE: 1

Tyr Thr Arg Leu His His Trp Ile Pro Pro Gln Arg
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic

<400> SEQUENCE: 2

Val Thr Pro Leu Leu Lys Phe Arg Ala Leu Ser Ser
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic

<400> SEQUENCE: 3

Ala His Pro Trp Arg Tyr Thr Glu Pro Trp Ser Trp
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic

<400> SEQUENCE: 4

Ala Leu Ser Arg His His His Pro Ile Phe Pro Arg
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic

<400> SEQUENCE: 5

Asn Glu Val Val Pro Phe Ser Tyr Ala Arg Gln Ser
1               5                   10

<210> SEQ ID NO 6
<211> LENGTH: 12
<212> TYPE: PRT
<213> ORGANISM: Artificial
<220> FEATURE:
```

<223> OTHER INFORMATION: Synthetic

<400> SEQUENCE: 6

His Val Pro His Leu Ala Ser Ile Met Ala Ser Asn
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic

<400> SEQUENCE: 7

His Trp Gly Leu His Leu Ser Ala Trp Ser Gln Met
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic

<400> SEQUENCE: 8

His Trp Lys Pro Trp Thr Ser Pro Ser Arg His Ser
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic

<400> SEQUENCE: 9

Ile Asp Lys Pro Leu His Val Val Leu Ala Leu Gly
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Ser Pro Cys Ala Tyr Thr Ser Thr Cys Asp Ala Leu
1               5                   10

<210> SEQ ID NO 11
<211> LENGTH: 11
<212> TYPE: PRT
<213> ORGANISM: Artificial
<220> FEATURE:
<223> OTHER INFORMATION: Synthetic

<400> SEQUENCE: 11

Ser Tyr Ser Pro Asn Leu Lys Ser Ala Tyr Asn
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic

```
<400> SEQUENCE: 12

Thr His His Pro Thr Glu Tyr Leu Thr Arg Ala Pro
1               5                   10

<210> SEQ ID NO 13
<211> LENGTH: 12
<212> TYPE: PRT
<213> ORGANISM: Artificial
<220> FEATURE:
<223> OTHER INFORMATION: Synthetic

<400> SEQUENCE: 13

Thr Pro His Gln Asn Pro Trp Phe Phe Glu Ile Thr
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic

<400> SEQUENCE: 14

Thr Gln Trp His Asp Asp Ser Thr Phe Tyr Trp Leu
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Thr Val Asn Thr Tyr Tyr Asn Tyr Gly Met Ser Pro
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic

<400> SEQUENCE: 16

Thr Trp His Ala Ser Ala Pro Arg Pro Pro Leu Leu
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic

<400> SEQUENCE: 17

Val Thr Pro Leu Leu Lys Phe Arg Ala Leu Ser Ser
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic
```

```
<400> SEQUENCE: 18

Ala Ala Ala Pro Leu Asn Leu Ser Met Thr Phe Pro
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic

<400> SEQUENCE: 19

Ala Ala Leu Thr Phe Pro Ala Pro Gln Ser Ala Ser
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic

<400> SEQUENCE: 20

Ala Leu Val Pro Lys Asn Leu Thr Pro Pro Gln His
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic

<400> SEQUENCE: 21

Ala Asn Trp Ser Pro Trp His His Tyr His His Lys
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic

<400> SEQUENCE: 22

Ala Pro Ala His Pro His Thr Ala Tyr Pro Ser Gly
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic

<400> SEQUENCE: 23

Ala Thr Trp His Ser Phe Phe Tyr His Asn His Ser
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic

<400> SEQUENCE: 24
```

Ala Tyr Ser His Ser Thr Pro Ser Ser Leu Thr Glu
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

Asp Asp Asn Asn Leu Phe Trp Trp Asn Asn Ala Gln
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic

<400> SEQUENCE: 26

Asp Gly Met Phe Asn Tyr Arg Ala Ser Leu Asp Pro
1               5                   10

<210> SEQ ID NO 27
<211> LENGTH: 12
<212> TYPE: PRT
<213> ORGANISM: Artificial
<220> FEATURE:
<223> OTHER INFORMATION: Synthetic

<400> SEQUENCE: 27

Asp Leu His Gly Arg Thr Ser Ser Thr Pro Pro Asp
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic

<400> SEQUENCE: 28

Asp Pro Leu Gln Pro Pro Asp Asn Val Thr Tyr Phe
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic

<400> SEQUENCE: 29

Asp Gln Ala Ala Ser Arg Ser His Ser Phe Pro Leu
1               5                   10

<210> SEQ ID NO 30
<211> LENGTH: 12
<212> TYPE: PRT
<213> ORGANISM: Artificial
<220> FEATURE:
<223> OTHER INFORMATION: Synthetic

<400> SEQUENCE: 30

```
Glu His Gly Ser Ala Leu Phe Arg Trp Ser Gln Thr
1               5                   10
```

<210> SEQ ID NO 31
<211> LENGTH: 12
<212> TYPE: PRT
<213> ORGANISM: Artificial
<220> FEATURE:
<223> OTHER INFORMATION: Synthetic

<400> SEQUENCE: 31

```
Glu Val Phe His Trp Thr Ala Gly Thr Pro Arg Glu
1               5                   10
```

<210> SEQ ID NO 32
<211> LENGTH: 12
<212> TYPE: PRT
<213> ORGANISM: Artificial
<220> FEATURE:
<223> OTHER INFORMATION: Synthetic

<400> SEQUENCE: 32

```
Phe His Ser Ser Glu Ser Arg Pro Met Ser Pro Thr
1               5                   10
```

<210> SEQ ID NO 33
<211> LENGTH: 12
<212> TYPE: PRT
<213> ORGANISM: Artificial
<220> FEATURE:
<223> OTHER INFORMATION: Synthetic

<400> SEQUENCE: 33

```
Phe Gln Ser Val Pro Ser Lys Asn Ile Ala Thr His
1               5                   10
```

<210> SEQ ID NO 34
<211> LENGTH: 12
<212> TYPE: PRT
<213> ORGANISM: Artificial
<220> FEATURE:
<223> OTHER INFORMATION: Synthetic

<400> SEQUENCE: 34

```
Gly His His His Pro Ser Ala Thr Phe Asn Ala Arg
1               5                   10
```

<210> SEQ ID NO 35
<211> LENGTH: 12
<212> TYPE: PRT
<213> ORGANISM: Artificial
<220> FEATURE:
<223> OTHER INFORMATION: Synthetic

<400> SEQUENCE: 35

```
Gly His Ser Ala Ser Phe Ala Leu His Ser Ser Asp
1               5                   10
```

<210> SEQ ID NO 36
<211> LENGTH: 12
<212> TYPE: PRT
<213> ORGANISM: Artificial
<220> FEATURE:
<223> OTHER INFORMATION: Synthetic

<400> SEQUENCE: 36

```
Gly Leu Thr Ser Val Lys His His His Asn Ala His
```

```
1               5                   10
```

<210> SEQ ID NO 37
<211> LENGTH: 12
<212> TYPE: PRT
<213> ORGANISM: Artificial
<220> FEATURE:
<223> OTHER INFORMATION: Synthetic

<400> SEQUENCE: 37

```
Gly Met Asp Phe Arg Thr Leu Ile Trp Pro His Lys
1               5                   10
```

<210> SEQ ID NO 38
<211> LENGTH: 12
<212> TYPE: PRT
<213> ORGANISM: Artificial
<220> FEATURE:
<223> OTHER INFORMATION: Synthetic

<400> SEQUENCE: 38

```
Gly Met His Val Pro Gln Ile Pro Gly His Phe Leu
1               5                   10
```

<210> SEQ ID NO 39
<211> LENGTH: 12
<212> TYPE: PRT
<213> ORGANISM: Artificial
<220> FEATURE:
<223> OTHER INFORMATION: Synthetic

<400> SEQUENCE: 39

```
Gly Thr Ile Gly Pro Phe Pro Glu Thr Leu Arg Leu
1               5                   10
```

<210> SEQ ID NO 40
<211> LENGTH: 12
<212> TYPE: PRT
<213> ORGANISM: Artificial
<220> FEATURE:
<223> OTHER INFORMATION: Synthetic

<400> SEQUENCE: 40

```
His Gly Pro His Asp Met Thr Ile Val Gly Met Gly
1               5                   10
```

<210> SEQ ID NO 41
<211> LENGTH: 12
<212> TYPE: PRT
<213> ORGANISM: Artificial
<220> FEATURE:
<223> OTHER INFORMATION: Synthetic

<400> SEQUENCE: 41

```
His His Leu Phe Gln Ile His Pro Asp Ser Trp Pro
1               5                   10
```

<210> SEQ ID NO 42
<211> LENGTH: 12
<212> TYPE: PRT
<213> ORGANISM: Artificial
<220> FEATURE:
<223> OTHER INFORMATION: Synthetic

<400> SEQUENCE: 42

```
His His Tyr Lys Thr Asp Leu His Arg Thr Pro Arg
1               5                   10
```

```
<210> SEQ ID NO 43
<211> LENGTH: 12
<212> TYPE: PRT
<213> ORGANISM: Artificial
<220> FEATURE:
<223> OTHER INFORMATION: Synthetic

<400> SEQUENCE: 43

His Leu Lys His Leu Asn Trp Thr Ala Ser Lys Leu
1               5                   10

<210> SEQ ID NO 44
<211> LENGTH: 7
<212> TYPE: PRT
<213> ORGANISM: Artificial
<220> FEATURE:
<223> OTHER INFORMATION: Synthetic

<400> SEQUENCE: 44

His Leu Pro Lys Ser Leu Ser
1               5

<210> SEQ ID NO 45
<211> LENGTH: 12
<212> TYPE: PRT
<213> ORGANISM: Artificial
<220> FEATURE:
<223> OTHER INFORMATION: Synthetic

<400> SEQUENCE: 45

His Met Lys Ser Gln Thr Asp Thr Pro Phe Tyr Gly
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic

<400> SEQUENCE: 46

His Gln Met Phe Leu Ile Gly Thr Gly His Trp Gly
1               5                   10

<210> SEQ ID NO 47
<211> LENGTH: 12
<212> TYPE: PRT
<213> ORGANISM: Artificial
<220> FEATURE:
<223> OTHER INFORMATION: Synthetic

<400> SEQUENCE: 47

His Thr Leu His His Met Thr Thr Ser Pro Phe Ala
1               5                   10

<210> SEQ ID NO 48
<211> LENGTH: 12
<212> TYPE: PRT
<213> ORGANISM: Artificial
<220> FEATURE:
<223> OTHER INFORMATION: Synthetic

<400> SEQUENCE: 48

His Thr Asn Leu Met Gln Thr Thr Arg Pro Leu Val
1               5                   10
```

<210> SEQ ID NO 49
<211> LENGTH: 12
<212> TYPE: PRT
<213> ORGANISM: Artificial
<220> FEATURE:
<223> OTHER INFORMATION: Synthetic

<400> SEQUENCE: 49

His Val His Gln His Arg His Leu Val Glu Val Ile
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic

<400> SEQUENCE: 50

His Trp Leu Pro Leu Leu Gly Gly Glu Leu Ser Ala
1               5                   10

<210> SEQ ID NO 51
<211> LENGTH: 12
<212> TYPE: PRT
<213> ORGANISM: Artificial
<220> FEATURE:
<223> OTHER INFORMATION: Synthetic

<400> SEQUENCE: 51

His Tyr Phe Ser Arg Thr Gln Thr Leu Ser Thr Leu
1               5                   10

<210> SEQ ID NO 52
<211> LENGTH: 12
<212> TYPE: PRT
<213> ORGANISM: Artificial
<220> FEATURE:
<223> OTHER INFORMATION: Synthetic

<400> SEQUENCE: 52

His Tyr Gln Phe His Trp Arg Ser Leu Ser Gly Pro
1               5                   10

<210> SEQ ID NO 53
<211> LENGTH: 12
<212> TYPE: PRT
<213> ORGANISM: Artificial
<220> FEATURE:
<223> OTHER INFORMATION: Synthetic

<400> SEQUENCE: 53

Ile His Arg Ala Pro Thr Pro Phe Asn Leu Gly Thr
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic

<400> SEQUENCE: 54

Ile Ile Pro Leu Arg Met Asn Thr Ala Tyr Pro Tyr
1               5                   10

<210> SEQ ID NO 55
<211> LENGTH: 12
<212> TYPE: PRT
<213> ORGANISM: Artificial
<220> FEATURE:
<223> OTHER INFORMATION: Synthetic

<400> SEQUENCE: 55

Ile Pro Phe Ala Thr Ala Ala Tyr Asn Ala Pro Gly
1               5                   10

<210> SEQ ID NO 56
<211> LENGTH: 12
<212> TYPE: PRT
<213> ORGANISM: Artificial
<220> FEATURE:
<223> OTHER INFORMATION: Synthetic

<400> SEQUENCE: 56

Lys Ala Tyr Leu Asp Ser Ile Pro Ile Thr Pro Arg
1               5                   10

<210> SEQ ID NO 57
<211> LENGTH: 12
<212> TYPE: PRT
<213> ORGANISM: Artificial
<220> FEATURE:
<223> OTHER INFORMATION: Synthetic

<400> SEQUENCE: 57

Lys Val Thr Thr Asn Tyr Ala Leu His Leu Ala Ser
1               5                   10

<210> SEQ ID NO 58
<211> LENGTH: 12
<212> TYPE: PRT
<213> ORGANISM: Artificial
<220> FEATURE:
<223> OTHER INFORMATION: Synthetic

<400> SEQUENCE: 58

Leu Pro Phe Pro Leu Ser Tyr Asn Ile Gly Pro Ala
1               5                   10

<210> SEQ ID NO 59
<211> LENGTH: 12
<212> TYPE: PRT
<213> ORGANISM: Artificial
<220> FEATURE:
<223> OTHER INFORMATION: Synthetic

<400> SEQUENCE: 59

Leu Pro Pro Pro Pro His Leu Pro Thr Phe Leu Pro
1               5                   10

<210> SEQ ID NO 60
<211> LENGTH: 12
<212> TYPE: PRT
<213> ORGANISM: Artificial
<220> FEATURE:
<223> OTHER INFORMATION: Synthetic

<400> SEQUENCE: 60

Leu Pro Thr Phe Asn Phe Ser Leu Pro Gly Ile Ile
1               5                   10

<210> SEQ ID NO 61

```
<211> LENGTH: 12
<212> TYPE: PRT
<213> ORGANISM: Artificial
<220> FEATURE:
<223> OTHER INFORMATION: Synthetic

<400> SEQUENCE: 61

Leu Ser Thr His Lys Leu Phe His Ser His Ser Gln
1               5                   10

<210> SEQ ID NO 62
<211> LENGTH: 12
<212> TYPE: PRT
<213> ORGANISM: Artificial
<220> FEATURE:
<223> OTHER INFORMATION: Synthetic

<400> SEQUENCE: 62

Met Asp Thr Pro Gly His Leu His Leu Ser Arg Ser
1               5                   10

<210> SEQ ID NO 63
<211> LENGTH: 11
<212> TYPE: PRT
<213> ORGANISM: Artificial
<220> FEATURE:
<223> OTHER INFORMATION: Synthetic

<400> SEQUENCE: 63

Met Lys Glu Ala Pro His Asp Gly Ser Cys Leu
1               5                   10

<210> SEQ ID NO 64
<211> LENGTH: 12
<212> TYPE: PRT
<213> ORGANISM: Artificial
<220> FEATURE:
<223> OTHER INFORMATION: Synthetic

<400> SEQUENCE: 64

Asn Phe Ala Gln Asn Leu Ser Ser Asn Thr Tyr Trp
1               5                   10

<210> SEQ ID NO 65
<211> LENGTH: 12
<212> TYPE: PRT
<213> ORGANISM: Artificial
<220> FEATURE:
<223> OTHER INFORMATION: Synthetic

<400> SEQUENCE: 65

Asn Gly Tyr Leu Gly Leu Arg Pro Gln Leu His Phe
1               5                   10

<210> SEQ ID NO 66
<211> LENGTH: 12
<212> TYPE: PRT
<213> ORGANISM: Artificial
<220> FEATURE:
<223> OTHER INFORMATION: Synthetic

<400> SEQUENCE: 66

Asn His Leu Asn Ser Met Ser Ser Val Glu Ala Leu
1               5                   10

<210> SEQ ID NO 67
<211> LENGTH: 12
```

<212> TYPE: PRT
<213> ORGANISM: Artificial
<220> FEATURE:
<223> OTHER INFORMATION: Synthetic

<400> SEQUENCE: 67

Asn His Gln Leu His Gln Asn His Phe Pro Arg Met
1               5                   10

<210> SEQ ID NO 68
<211> LENGTH: 12
<212> TYPE: PRT
<213> ORGANISM: Artificial
<220> FEATURE:
<223> OTHER INFORMATION: Synthetic

<400> SEQUENCE: 68

Asn Leu Thr His Pro Leu Trp Gly Pro Asp Leu Phe
1               5                   10

<210> SEQ ID NO 69
<211> LENGTH: 12
<212> TYPE: PRT
<213> ORGANISM: Artificial
<220> FEATURE:
<223> OTHER INFORMATION: Synthetic

<400> SEQUENCE: 69

Asn Thr Leu Ser Gln Pro Arg Val Gly Gly Leu Asn
1               5                   10

<210> SEQ ID NO 70
<211> LENGTH: 12
<212> TYPE: PRT
<213> ORGANISM: Artificial
<220> FEATURE:
<223> OTHER INFORMATION: Synthetic

<400> SEQUENCE: 70

Asn Thr Pro Pro Met Ser His Gln Asn Pro Val Arg
1               5                   10

<210> SEQ ID NO 71
<211> LENGTH: 12
<212> TYPE: PRT
<213> ORGANISM: Artificial
<220> FEATURE:
<223> OTHER INFORMATION: Synthetic

<400> SEQUENCE: 71

Gln Asp Ala Leu Thr Pro Arg Arg Leu Trp Pro Thr
1               5                   10

<210> SEQ ID NO 72
<211> LENGTH: 12
<212> TYPE: PRT
<213> ORGANISM: Artificial
<220> FEATURE:
<223> OTHER INFORMATION: Synthetic

<400> SEQUENCE: 72

Gln Ile Leu Gly Tyr Pro Thr Asn Leu Gly Pro Phe
1               5                   10

<210> SEQ ID NO 73
<211> LENGTH: 12
<212> TYPE: PRT

```
<213> ORGANISM: Artificial
<220> FEATURE:
<223> OTHER INFORMATION: Synthetic

<400> SEQUENCE: 73

Gln Tyr Asp Thr His Arg Gly Ser Asp Asn Lys Gln
1               5                   10

<210> SEQ ID NO 74
<211> LENGTH: 12
<212> TYPE: PRT
<213> ORGANISM: Artificial
<220> FEATURE:
<223> OTHER INFORMATION: Synthetic

<400> SEQUENCE: 74

Arg His Leu Glu Ile Asn His Val Thr Leu Leu Val
1               5                   10

<210> SEQ ID NO 75
<211> LENGTH: 12
<212> TYPE: PRT
<213> ORGANISM: Artificial
<220> FEATURE:
<223> OTHER INFORMATION: Synthetic

<400> SEQUENCE: 75

Ser Ala His Thr Leu Ala Ala Trp Phe Ala Lys Pro
1               5                   10

<210> SEQ ID NO 76
<211> LENGTH: 12
<212> TYPE: PRT
<213> ORGANISM: Artificial
<220> FEATURE:
<223> OTHER INFORMATION: Synthetic

<400> SEQUENCE: 76

Ser Glu Thr Leu Gln Val Tyr Lys Pro Ile Leu Val
1               5                   10

<210> SEQ ID NO 77
<211> LENGTH: 11
<212> TYPE: PRT
<213> ORGANISM: Artificial
<220> FEATURE:
<223> OTHER INFORMATION: Synthetic

<400> SEQUENCE: 77

Ser His Val Leu Ser Ser Pro Ser Arg Gly Val
1               5                   10

<210> SEQ ID NO 78
<211> LENGTH: 12
<212> TYPE: PRT
<213> ORGANISM: Artificial
<220> FEATURE:
<223> OTHER INFORMATION: Synthetic

<400> SEQUENCE: 78

Ser His Ser Thr Gln Asp Arg Phe Val His Pro Ala
1               5                   10

<210> SEQ ID NO 79
<211> LENGTH: 12
<212> TYPE: PRT
<213> ORGANISM: Artificial
```

<220> FEATURE:
<223> OTHER INFORMATION: Synthetic

<400> SEQUENCE: 79

Ser His Tyr Pro Thr Ala Arg Gln Leu Thr Asn Ser
1               5                   10

<210> SEQ ID NO 80
<211> LENGTH: 12
<212> TYPE: PRT
<213> ORGANISM: Artificial
<220> FEATURE:
<223> OTHER INFORMATION: Synthetic

<400> SEQUENCE: 80

Ser Ile Ala Pro His Ser Gln Arg Leu Ser Leu Ser
1               5                   10

<210> SEQ ID NO 81
<211> LENGTH: 12
<212> TYPE: PRT
<213> ORGANISM: Artificial
<220> FEATURE:
<223> OTHER INFORMATION: Synthetic

<400> SEQUENCE: 81

Ser Leu Pro Asp Ile Ser Thr Arg Gly Leu Ala Ala
1               5                   10

<210> SEQ ID NO 82
<211> LENGTH: 12
<212> TYPE: PRT
<213> ORGANISM: Artificial
<220> FEATURE:
<223> OTHER INFORMATION: Synthetic

<400> SEQUENCE: 82

Ser Pro Pro His Pro Ala Arg Tyr Tyr Ser Pro Leu
1               5                   10

<210> SEQ ID NO 83
<211> LENGTH: 12
<212> TYPE: PRT
<213> ORGANISM: Artificial
<220> FEATURE:
<223> OTHER INFORMATION: Synthetic

<400> SEQUENCE: 83

Ser Pro Pro Thr Thr Met Thr Pro Asn Asn Met Pro
1               5                   10

<210> SEQ ID NO 84
<211> LENGTH: 12
<212> TYPE: PRT
<213> ORGANISM: Artificial
<220> FEATURE:
<223> OTHER INFORMATION: Synthetic

<400> SEQUENCE: 84

Ser Ser His Pro Ile Pro Tyr Asn Ala Ser Gln Met
1               5                   10

<210> SEQ ID NO 85
<211> LENGTH: 12
<212> TYPE: PRT
<213> ORGANISM: Artificial
<220> FEATURE:

```
<223> OTHER INFORMATION: Synthetic

<400> SEQUENCE: 85

Ser Thr Tyr Lys Asp Ser Trp Asn Glu Tyr Gly Pro
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic

<400> SEQUENCE: 86

Ser Tyr Gln Gln Pro Met Gly Leu Tyr Arg Gln Phe
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic

<400> SEQUENCE: 87

Thr Gly Leu Leu Gln Glu Pro Thr Phe Arg Gly Met
1               5                   10

<210> SEQ ID NO 88
<211> LENGTH: 12
<212> TYPE: PRT
<213> ORGANISM: Artificial
<220> FEATURE:
<223> OTHER INFORMATION: Synthetic

<400> SEQUENCE: 88

Thr His Gly His Tyr Tyr Pro Ser Ile Ala Leu Ser
1               5                   10

<210> SEQ ID NO 89
<211> LENGTH: 12
<212> TYPE: PRT
<213> ORGANISM: Artificial
<220> FEATURE:
<223> OTHER INFORMATION: Synthetic

<400> SEQUENCE: 89

Thr Leu Pro Ala Ala Ala Leu Pro Trp Leu Tyr Leu
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic

<400> SEQUENCE: 90

Thr Met Ile Pro Leu Ile Tyr Pro Pro Gln Ala Asn
1               5                   10

<210> SEQ ID NO 91
<211> LENGTH: 12
<212> TYPE: PRT
<213> ORGANISM: Artificial
<220> FEATURE:
<223> OTHER INFORMATION: Synthetic
```

```
<400> SEQUENCE: 91

Thr Pro Asp Leu Ser Gln Ser Ser Pro His Ser Phe
1               5                   10

<210> SEQ ID NO 92
<211> LENGTH: 12
<212> TYPE: PRT
<213> ORGANISM: Artificial
<220> FEATURE:
<223> OTHER INFORMATION: Synthetic

<400> SEQUENCE: 92

Thr Pro His Leu Pro Pro Thr Arg Ala Gly Ser Pro
1               5                   10

<210> SEQ ID NO 93
<211> LENGTH: 12
<212> TYPE: PRT
<213> ORGANISM: Artificial
<220> FEATURE:
<223> OTHER INFORMATION: Synthetic

<400> SEQUENCE: 93

Thr Pro Asn Pro Leu Gly Thr Gln Cys Met Thr Cys
1               5                   10

<210> SEQ ID NO 94
<211> LENGTH: 12
<212> TYPE: PRT
<213> ORGANISM: Artificial
<220> FEATURE:
<223> OTHER INFORMATION: Synthetic

<400> SEQUENCE: 94

Thr Gln Tyr Ile His Thr Asp Leu Ser Ser Thr Ser
1               5                   10

<210> SEQ ID NO 95
<211> LENGTH: 12
<212> TYPE: PRT
<213> ORGANISM: Artificial
<220> FEATURE:
<223> OTHER INFORMATION: Synthetic

<400> SEQUENCE: 95

Thr Ser His Gln Ile Tyr Pro Val Ser Trp Met Arg
1               5                   10

<210> SEQ ID NO 96
<211> LENGTH: 12
<212> TYPE: PRT
<213> ORGANISM: Artificial
<220> FEATURE:
<223> OTHER INFORMATION: Synthetic

<400> SEQUENCE: 96

Thr Ser Ser Ala Ser His Thr Asn Leu Thr Thr Arg
1               5                   10

<210> SEQ ID NO 97
<211> LENGTH: 12
<212> TYPE: PRT
<213> ORGANISM: Artificial
<220> FEATURE:
<223> OTHER INFORMATION: Synthetic
```

```
<400> SEQUENCE: 97

Thr Ser Thr Arg Asp Ile Trp Ser Thr His Asp Leu
1               5                   10

<210> SEQ ID NO 98
<211> LENGTH: 12
<212> TYPE: PRT
<213> ORGANISM: Artificial
<220> FEATURE:
<223> OTHER INFORMATION: Synthetic

<400> SEQUENCE: 98

Thr Ser Tyr Leu Asn Ser Gly Met Ile Pro Ala Arg
1               5                   10

<210> SEQ ID NO 99
<211> LENGTH: 12
<212> TYPE: PRT
<213> ORGANISM: Artificial
<220> FEATURE:
<223> OTHER INFORMATION: Synthetic

<400> SEQUENCE: 99

Thr Thr His Ser Glu Leu Ser Gly Tyr Val Glu Leu
1               5                   10

<210> SEQ ID NO 100
<211> LENGTH: 12
<212> TYPE: PRT
<213> ORGANISM: Artificial
<220> FEATURE:
<223> OTHER INFORMATION: Synthetic

<400> SEQUENCE: 100

Val Glu Ala Glu Asn Asp Ser Gly Met Asn Ser Gln
1               5                   10

<210> SEQ ID NO 101
<211> LENGTH: 12
<212> TYPE: PRT
<213> ORGANISM: Artificial
<220> FEATURE:
<223> OTHER INFORMATION: Synthetic

<400> SEQUENCE: 101

Val Phe Asp Leu Asn Gly Tyr Asn Arg Asn Pro Ile
1               5                   10

<210> SEQ ID NO 102
<211> LENGTH: 12
<212> TYPE: PRT
<213> ORGANISM: Artificial
<220> FEATURE:
<223> OTHER INFORMATION: Synthetic

<400> SEQUENCE: 102

Val Gly Asn Met Pro Phe Val His Pro His Gln Trp
1               5                   10

<210> SEQ ID NO 103
<211> LENGTH: 12
<212> TYPE: PRT
<213> ORGANISM: Artificial
<220> FEATURE:
<223> OTHER INFORMATION: Synthetic

<400> SEQUENCE: 103
```

```
Val Pro Ala Thr Arg Val Ser Pro Thr Pro Tyr Ala
1               5                   10
```

<210> SEQ ID NO 104
<211> LENGTH: 12
<212> TYPE: PRT
<213> ORGANISM: Artificial
<220> FEATURE:
<223> OTHER INFORMATION: Synthetic

<400> SEQUENCE: 104

```
Val Ser His Pro Pro Arg Phe Pro Gly Trp Pro Gln
1               5                   10
```

<210> SEQ ID NO 105
<211> LENGTH: 12
<212> TYPE: PRT
<213> ORGANISM: Artificial
<220> FEATURE:
<223> OTHER INFORMATION: Synthetic

<400> SEQUENCE: 105

```
Trp His Glu Pro Ser Thr Trp Leu Val Asn Pro Arg
1               5                   10
```

<210> SEQ ID NO 106
<211> LENGTH: 12
<212> TYPE: PRT
<213> ORGANISM: Artificial
<220> FEATURE:
<223> OTHER INFORMATION: Synthetic

<400> SEQUENCE: 106

```
Trp Pro Ala His Pro His Thr Ala Tyr Pro Ser Gly
1               5                   10
```

<210> SEQ ID NO 107
<211> LENGTH: 12
<212> TYPE: PRT
<213> ORGANISM: Artificial
<220> FEATURE:
<223> OTHER INFORMATION: Synthetic

<400> SEQUENCE: 107

```
Trp Pro Ile Asn Gln Gln Arg Gln Leu Tyr Thr Ser
1               5                   10
```

<210> SEQ ID NO 108
<211> LENGTH: 12
<212> TYPE: PRT
<213> ORGANISM: Artificial
<220> FEATURE:
<223> OTHER INFORMATION: Synthetic

<400> SEQUENCE: 108

```
Trp Ser Asp Pro Arg Ala Val Thr Trp Arg Ala His
1               5                   10
```

<210> SEQ ID NO 109
<211> LENGTH: 12
<212> TYPE: PRT
<213> ORGANISM: Artificial
<220> FEATURE:
<223> OTHER INFORMATION: Synthetic

<400> SEQUENCE: 109

Trp Ser Leu Thr Pro Thr Ala Leu Leu Thr Ser Phe
1               5                   10

<210> SEQ ID NO 110
<211> LENGTH: 12
<212> TYPE: PRT
<213> ORGANISM: Artificial
<220> FEATURE:
<223> OTHER INFORMATION: Synthetic

<400> SEQUENCE: 110

Trp Ser Val Pro Leu Pro Pro Gly Asp Pro Lys Pro
1               5                   10

<210> SEQ ID NO 111
<211> LENGTH: 12
<212> TYPE: PRT
<213> ORGANISM: Artificial
<220> FEATURE:
<223> OTHER INFORMATION: Synthetic

<400> SEQUENCE: 111

Tyr Met Ala Pro His Val Pro Leu Thr Asn Ala Ser
1               5                   10

<210> SEQ ID NO 112
<211> LENGTH: 12
<212> TYPE: PRT
<213> ORGANISM: Artificial
<220> FEATURE:
<223> OTHER INFORMATION: Synthetic

<400> SEQUENCE: 112

Tyr Pro Asn Pro Trp His Glu Ser Ser Phe Met Ser
1               5                   10

<210> SEQ ID NO 113
<211> LENGTH: 251
<212> TYPE: PRT
<213> ORGANISM: Artificial Sequence
<220> FEATURE:
<223> OTHER INFORMATION: Synthetic

<400> SEQUENCE: 113

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Asp Ile Lys Arg Ser Gly Gly Ser
            100                 105                 110

Thr Ile Thr Ser Tyr Asn Val Tyr Tyr Thr Lys Leu Ser Ser Ser Gly
        115                 120                 125

Thr Glu Val Gln Leu Val Gln Ser Gly Ala Glu Val Lys Lys Pro Gly
    130                 135                 140

```
Ser Ser Val Lys Val Ser Cys Lys Ala Ser Gly Gly Thr Phe Ser Ser
145                 150                 155                 160

Tyr Ala Ile Ser Trp Val Arg Gln Ala Pro Gly Gln Gly Leu Glu Trp
                165                 170                 175

Met Gly Gly Ile Ile Pro Ile Phe Gly Thr Ala Asn Tyr Ala Gln Lys
                180                 185                 190

Phe Gln Gly Arg Val Thr Ile Thr Ala Asp Glu Ser Thr Ser Thr Ala
            195                 200                 205

Tyr Met Glu Leu Ser Ser Leu Arg Ser Glu Asp Thr Ala Val Tyr Tyr
        210                 215                 220

Cys Ala Arg Asp Pro Glu Asp Asn Trp Gly Ala Phe Asp Ile Trp Gly
225                 230                 235                 240

Gln Gly Thr Met Val Thr Val Ser Ser Ala Ser
                245                 250
```

<210> SEQ ID NO 114
<211> LENGTH: 250
<212> TYPE: PRT
<213> ORGANISM: Artificial Sequence
<220> FEATURE:
<223> OTHER INFORMATION: Synthetic

<400> SEQUENCE: 114

```
Glu Ile Val Met Thr Gln Ser Pro Gly Thr Leu Ser Leu Ser Pro Gly
1               5                   10                  15

Asp Arg Ala Thr Leu Ser Cys Arg Ala Ser Gln Ser Val Ser Gly Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Thr Leu Pro
                85                  90                  95

Thr Phe Gly Gln Gly Thr Lys Leu Glu Ile Lys Arg Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Gln Ser Gly Gly Gly Val Val Gln Pro Gly
130                 135                 140

Arg Pro Leu Lys Leu Ser Cys Ala Ala Ser Gly Phe Thr Phe Ser Ser
145                 150                 155                 160

Tyr Ala Met His Trp Val Arg Gln Ala Pro Gly Lys Gly Leu Glu Trp
                165                 170                 175

Val Ala Val Ile Ser Tyr Asp Gly Ser Asn Lys Tyr Tyr Ala Asp Ser
                180                 185                 190

Val Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
        210                 215                 220

Cys Ala Arg Asp Leu Ser Trp Asn Asp Ala Phe Asp Ile Trp Gly Gln
225                 230                 235                 240

Gly Thr Met Val Thr Val Ser Ser Ala Ser
                245                 250
```

<210> SEQ ID NO 115
<211> LENGTH: 240
<212> TYPE: PRT
<213> ORGANISM: Artificial Sequence
<220> FEATURE:
<223> OTHER INFORMATION: Synthetic

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Met Ile Thr Pro Leu Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Gly Val Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Thr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Asn Asp
    210                 215                 220

Ser Phe Pro Thr Thr Phe Gly Gln Gly Thr Lys Val Glu Ile Lys Arg
225                 230                 235                 240
```

<210> SEQ ID NO 116
<211> LENGTH: 239
<212> TYPE: PRT
<213> ORGANISM: Artificial Sequence
<220> FEATURE:
<223> OTHER INFORMATION: Synthetic

<400> SEQUENCE: 116

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser His Ile Gln Gly Gln Gly Arg Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Thr His Gly Lys Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Ser
    210                 215                 220

Gly Val Pro Thr Thr Phe Gly Gln Gly Thr Lys Val Glu Ile Lys
225                 230                 235

<210> SEQ ID NO 117
<211> LENGTH: 52
<212> TYPE: PRT
<213> ORGANISM: Artificial Sequence
<220> FEATURE:
<223> OTHER INFORMATION: Synthetic

<400> SEQUENCE: 117

Gln Gly Gly Cys Gln Ser Pro Ala Pro Ser Cys Ser Trp Ala Trp Cys
1               5                   10                  15

Trp His Pro Trp Thr Trp Ser Trp Cys Arg Arg Pro Trp Thr Trp Ser
            20                  25                  30

Trp Cys Trp Cys Ser Trp Thr Trp Ser Trp Cys Trp Cys Ser Trp Leu
        35                  40                  45

Arg Gly Ser Thr
    50

<210> SEQ ID NO 118
<211> LENGTH: 227
<212> TYPE: PRT
<213> ORGANISM: Artificial Sequence
<220> FEATURE:
<223> OTHER INFORMATION: Synthetic

<400> SEQUENCE: 118

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                    85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Gly Leu His Asn His Tyr Thr Gln Lys Ser Leu Ser Leu Ser
    210                 215                 220

Pro Gly Lys
225

<210> SEQ ID NO 119
<211> LENGTH: 15
<212> TYPE: PRT
<213> ORGANISM: Artificial Sequence
<220> FEATURE:
<223> OTHER INFORMATION: Synthetic

<400> SEQUENCE: 119

Met Tyr Ile Phe Pro Val His Trp Gln Phe Gly Gln Leu Asp Gln
1               5                   10                  15

<210> SEQ ID NO 120
<211> LENGTH: 12
<212> TYPE: PRT
<213> ORGANISM: Artificial Sequence
<220> FEATURE:
<223> OTHER INFORMATION: Synthetic

<400> SEQUENCE: 120

Lys Asn His Gly Ala Thr Arg Thr Thr Arg Ala Ser
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic

<400> SEQUENCE: 121

Tyr Thr Arg Leu His His Trp Ile Pro Pro Gln Arg
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Val Thr Pro Leu Leu Lys Phe Arg Ala Leu Ser Ser
```

```
1               5                   10
```

<210> SEQ ID NO 123
<211> LENGTH: 12
<212> TYPE: PRT
<213> ORGANISM: Artificial Sequence
<220> FEATURE:
<223> OTHER INFORMATION: Synthetic

<400> SEQUENCE: 123

```
Val Ser His Pro Pro Arg Phe Pro Gly Trp Pro Gln
1               5                   10
```

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

```
Lys Ala Tyr Leu Asp Ser Ile Pro Ile Thr Pro Arg
1               5                   10
```

<210> SEQ ID NO 125
<211> LENGTH: 12
<212> TYPE: PRT
<213> ORGANISM: Artificial Sequence
<220> FEATURE:
<223> OTHER INFORMATION: Synthetic

<400> SEQUENCE: 125

```
Thr Ser Tyr Leu Asn Ser Gly Met Ile Pro Ala Arg
1               5                   10
```

<210> SEQ ID NO 126
<211> LENGTH: 12
<212> TYPE: PRT
<213> ORGANISM: Artificial Sequence
<220> FEATURE:
<223> OTHER INFORMATION: Synthetic

<400> SEQUENCE: 126

```
Ala His Pro Trp Arg Tyr Thr Glu Pro Trp Ser Trp
1               5                   10
```

<210> SEQ ID NO 127
<211> LENGTH: 12
<212> TYPE: PRT
<213> ORGANISM: Artificial Sequence
<220> FEATURE:
<223> OTHER INFORMATION: Synthetic

<400> SEQUENCE: 127

```
Val Pro Ala Thr Arg Val Ser Pro Thr Pro Tyr Ala
1               5                   10
```

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

```
Gln Ile Leu Gly Tyr Pro Thr Asn Leu Gly Pro Phe
1               5                   10
```

<210> SEQ ID NO 129
<211> LENGTH: 12
<212> TYPE: PRT
<213> ORGANISM: Artificial Sequence
<220> FEATURE:
<223> OTHER INFORMATION: Synthetic

<400> SEQUENCE: 129

Ala His Pro Trp Arg Tyr Thr Glu Pro Trp Ser Trp
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic

<400> SEQUENCE: 130

Leu Ser Thr His Lys Leu Phe His Ser His Ser Gln
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic

<400> SEQUENCE: 131

Ala Ala Ala Pro Leu Asn Leu Ser Met Thr Phe Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Ile Asp Lys Pro Leu His Val Val Leu Ala Leu Gly
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic

<400> SEQUENCE: 133

Thr Gln Trp His Asp Asp Ser Thr Phe Tyr Trp Leu
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic

<400> SEQUENCE: 134

Thr Thr His Ser Glu Leu Ser Gly Tyr Val Glu Leu
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic

<400> SEQUENCE: 135

```
Ile Pro Phe Ala Thr Ala Ala Tyr Asn Ala Pro Gly
1               5                   10
```

<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

```
Val Gly Asn Met Pro Phe Val His Pro His Gln Trp
1               5                   10
```

<210> SEQ ID NO 137
<211> LENGTH: 12
<212> TYPE: PRT
<213> ORGANISM: Artificial Sequence
<220> FEATURE:
<223> OTHER INFORMATION: Synthetic

<400> SEQUENCE: 137

```
His Tyr Phe Ser Arg Thr Gln Thr Leu Ser Thr Leu
1               5                   10
```

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

```
Ser Ala His Thr Leu Ala Ala Trp Phe Ala Lys Pro
1               5                   10
```

<210> SEQ ID NO 139
<211> LENGTH: 12
<212> TYPE: PRT
<213> ORGANISM: Artificial Sequence
<220> FEATURE:
<223> OTHER INFORMATION: Synthetic

<400> SEQUENCE: 139

```
Tyr Ser Ala His Ile Gly Ser Arg His Thr His Tyr
1               5                   10
```

<210> SEQ ID NO 140
<211> LENGTH: 52
<212> TYPE: PRT
<213> ORGANISM: Artificial Sequence
<220> FEATURE:
<223> OTHER INFORMATION: Synthetic

<400> SEQUENCE: 140

```
Gln Gly Gly Cys Gln Ser Pro Ala Pro Cys Ser Trp Ala Trp Cys
1               5                   10                  15

Trp His Pro Trp Thr Trp Ser Trp Cys Arg Arg Pro Trp Thr Trp Ser
```

```
                    20                  25                  30
Trp Cys Trp Cys Ser Trp Thr Trp Ser Trp Cys Trp Cys Ser Trp Leu
        35                  40                  45

Arg Gly Ser Thr
        50

<210> SEQ ID NO 141
<211> LENGTH: 83
<212> TYPE: DNA
<213> ORGANISM: Artificial Sequence
<220> FEATURE:
<223> OTHER INFORMATION: Synthetic

<400> SEQUENCE: 141
tatacccgcc tgcatcattg gattccgccg cagcgcgaca aaactcacac atgcccaccg     60
tgcccagcac ctgaactcct ggg                                            83

<210> SEQ ID NO 142
<211> LENGTH: 27
<212> TYPE: PRT
<213> ORGANISM: Artificial Sequence
<220> FEATURE:
<223> OTHER INFORMATION: Synthetic

<400> SEQUENCE: 142

Tyr Thr Arg Leu His His Trp Ile Pro Pro Gln Arg Asp Lys Thr His
1               5                   10                  15

Thr Cys Pro Pro Cys Pro Ala Pro Glu Leu Leu
            20                  25

<210> SEQ ID NO 143
<211> LENGTH: 83
<212> TYPE: DNA
<213> ORGANISM: Artificial Sequence
<220> FEATURE:
<223> OTHER INFORMATION: Synthetic

<400> SEQUENCE: 143
gtgaccccgc tgctgaaatt tcgcgcgctg agcagcgaca aaactcacac atgcccaccg     60
tgcccagcac ctgaactcct ggg                                            83

<210> SEQ ID NO 144
<211> LENGTH: 27
<212> TYPE: PRT
<213> ORGANISM: Artificial Sequence
<220> FEATURE:
<223> OTHER INFORMATION: Synthetic

<400> SEQUENCE: 144

Val Thr Pro Leu Leu Lys Phe Arg Ala Leu Ser Ser Asp Lys Thr His
1               5                   10                  15

Thr Cys Pro Pro Cys Pro Ala Pro Glu Leu Leu
            20                  25

<210> SEQ ID NO 145
<211> LENGTH: 284
<212> TYPE: PRT
<213> ORGANISM: Artificial Sequence
<220> FEATURE:
<223> OTHER INFORMATION: Synthetic

<400> SEQUENCE: 145

Met Lys Lys Leu Leu Phe Ala Ile Pro Leu Val Val Pro Phe Tyr Ser
```

```
                1               5                  10                 15
          His Ser Thr Met Glu Glu Val Gln Leu Leu Glu Ser Gly Gly Gly Leu
                       20                  25                  30

Val Gln Pro Gly Gly Ser Leu Arg Leu Ser Cys Ala Ala Ser Gly Phe
                       35                  40                  45

Thr Phe Ser Ser Tyr Ala Met Ser Trp Val Arg Gln Ala Pro Gly Lys
                       50                  55                  60

Gly Leu Glu Trp Val Ser Met Ile Thr Pro Leu Gly Ser Thr Thr Ala
           65                  70                  75                  80

Tyr Ala Asp Ser Val Lys Gly Arg Phe Thr Ile Ser Arg Asp Asn Ser
                       85                  90                  95

Lys Asn Thr Leu Tyr Leu Gln Met Asn Ser Leu Arg Ala Glu Asp Thr
                       100                 105                 110

Ala Val Tyr Tyr Cys Ala Lys Arg Ala Gly Val Phe Asp Tyr Trp Gly
                       115                 120                 125

Gln Gly Thr Leu Val Thr Val Ser Ser Gly Gly Gly Ser Gly Gly
                       130                 135                 140

Gly Gly Ser Gly Gly Gly Ser Thr Asp Ile Gln Met Thr Gln Ser
           145                 150                 155                 160

Pro Ser Ser Leu Ser Ala Ser Val Gly Asp Arg Val Thr Ile Thr Cys
                       165                 170                 175

Arg Ala Ser Gln Ser Ile Ser Ser Tyr Leu Asn Trp Tyr Gln Gln Lys
                       180                 185                 190

Pro Gly Lys Ala Pro Lys Leu Leu Ile Tyr Arg Ala Ser Thr Leu Gln
                       195                 200                 205

Ser Gly Val Pro Ser Arg Phe Ser Gly Ser Gly Ser Gly Thr Asp Phe
           210                 215                 220

Thr Leu Thr Ile Ser Ser Leu Gln Pro Glu Asp Phe Ala Thr Tyr Tyr
           225                 230                 235                 240

Cys Gln Gln Asn Asp Ser Phe Pro Thr Thr Phe Gly Gln Gly Thr Lys
                       245                 250                 255

Val Glu Ile Lys Arg Phe Leu Glu Gln Lys Leu Ile Ser Glu Glu Asp
                       260                 265                 270

Leu Asn Ser Ala Val Asp His His His His His His
                       275                 280

<210> SEQ ID NO 146
<211> LENGTH: 297
<212> TYPE: PRT
<213> ORGANISM: Artificial Sequence
<220> FEATURE:
<223> OTHER INFORMATION: Synthetic

<400> SEQUENCE: 146

Met Lys Lys Leu Leu Phe Ala Ile Pro Leu Val Val Pro Phe Tyr Ser
 1               5                  10                  15

His Ser Thr Met Glu Ala Ile Arg Met Thr Gln Ser Pro Ser Ser Leu
                 20                  25                  30

Ser Ala Ser Val Gly Asp Arg Val Thr Ile Thr Cys Gln Ala Ser Gln
                 35                  40                  45

Asp Ile Ser Asn Tyr Leu Asn Trp Tyr Gln Gln Lys Pro Gly Lys Ala
                 50                  55                  60

Pro Lys Leu Leu Ile Tyr Asp Ala Ser Asn Leu Glu Thr Gly Val Pro
 65                  70                  75                  80

Ser Arg Phe Ser Gly Ser Gly Ser Gly Thr Asp Phe Thr Leu Thr Ile
```

-continued

```
                85                  90                  95
Ser Ser Leu Gln Pro Glu Asp Phe Ala Thr Tyr Tyr Cys Gln Gln Ser
            100                 105                 110

Tyr Ser Thr Pro Tyr Thr Phe Gly Gln Gly Thr Lys Leu Asp Ile Lys
            115                 120                 125

Arg Ser Gly Gly Ser Thr Ile Thr Ser Tyr Asn Val Tyr Tyr Thr Lys
            130                 135                 140

Leu Ser Ser Ser Gly Thr Glu Val Gln Leu Val Gln Ser Gly Ala Glu
145                 150                 155                 160

Val Lys Lys Pro Gly Ser Ser Val Lys Val Ser Cys Lys Ala Ser Gly
                165                 170                 175

Gly Thr Phe Ser Ser Tyr Ala Ile Ser Trp Val Arg Gln Ala Pro Gly
                180                 185                 190

Gln Gly Leu Glu Trp Met Gly Gly Ile Ile Pro Ile Phe Gly Thr Ala
            195                 200                 205

Asn Tyr Ala Gln Lys Phe Gln Gly Arg Val Thr Ile Thr Ala Asp Glu
            210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Asp Pro Glu Asp Asn Trp Gly Ala
                245                 250                 255

Phe Asp Ile Trp Gly Gln Gly Thr Met Val Thr Val Ser Ser Ala Ser
                260                 265                 270

Arg Ser Phe Leu Glu Gln Lys Leu Ile Ser Glu Glu Asp Leu Asn Ser
            275                 280                 285

Ala Val Asp His His His His His His
290                 295
```

SPARC BINDING SCFVS

PRIORITY CLAIM

This application is a divisional of U.S. patent application Ser. No. 14/451,858, filed Aug. 5, 2014, which issued as U.S. Pat. No. 9,314,537 on Apr. 19, 2016, which is a divisional of U.S. patent application Ser. No. 13/132,455, filed Sep. 26, 2011 which issued as U.S. Pat. No. 8,809,507 on Aug. 19, 2014, which is the national phase of International Patent Application No. PCT/US2009/067032, filed Dec. 7, 2009. The current application, claims the benefit of U.S. Provisional Application No. 61/120,228, filed on Dec. 5, 2008. The complete contents of U.S. patent application Ser. Nos. 14/451,858, 13/132,455 and 61/120,228 and PCT/US2009/067032, are hereby incorporated by reference.

STATEMENT REGARDING FEDERALLY SPONSORED RESEARCH AND DEVELOPMENT

None

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 45000 bytes ASCII (Text) file named Replacement-Sequence-Listing.

BACKGROUND OF THE INVENTION

Secreted Protein, Acidic, Rich in Cysteines (SPARC), also known as osteonectin, is a 303 amino acid glycoprotein which is expressed in the human body. SPARC expression is developmentally regulated, with SPARC being predominantly expressed in tissues undergoing remodeling during normal development or in response to injury. See, e.g., Lane et al., FASEB J., 8, 163-173 (1994). For example, high levels of SPARC protein are expressed in developing bones and teeth, principally osteoblasts, odontoblasts, perichondrial fibroblasts, and differentiating chondrocytes in murine, bovine, and human embryos. SPARC also plays important roles in cell-matrix interactions during tissue remodeling, wound repair, morphogenesis, cellular differentiation, cell migration, and angiogenesis, including where these processes are associated with disease states. For example, SPARC is expressed in renal interstitial fibrosis, and plays a role in the host response to pulmonary insults, such as bleomycin-induced pulmonary fibrosis.

SPARC is differentially expressed in tumors and its surrounding stroma in various cancers in comparison to the normal tissue, with the pattern depending on the type of cancer. Thus, there is no unifying model which explains all facets of its function and contribution to the development and progression of cancer. In one pattern, increased SPARC expression have been reported in breast cancer (Bellahcene and Castronovo, 1995; Jones et al., 2004; Lien et al., 2007; Porter et al., 1995), melanoma (Ledda et al., 1997a), and glioblastomas (Rempel et al., 1998). Increased SPARC expression plays a role in tumor promotion or progression in these cancers.

Accordingly, SPARC over expression in inflammation and some cancers makes a SPARC potential target for diagnosis and therapy.

BRIEF SUMMARY OF THE INVENTION

The invention provides compositions for delivering a therapeutic or diagnostic agent to a disease site in a mammal comprising a therapeutically or diagnostically effective amount of a pharmaceutical composition comprising the therapeutic or diagnostic agent coupled to a SPARC-binding-peptide ("SBP") and a pharmaceutically acceptable carrier ("inventive compositions"), including wherein the SBP comprises one or more of SEQ ID NOs: 1-117.

Particularly preferred embodiments include, e.g., inventive compositions for delivering a therapeutic agent to a disease site in a mammal comprising one or more SBPs, wherein the therapeutic agent is an antibody fragment comprising a functional antibody Fc domain, including, e.g., wherein the functional antibody Fc domain comprises SEQ ID NO: 118.

Additional preferred embodiments include inventive compositions for delivering a therapeutic or diagnostic agent to a disease site in a mammal composition, e.g., wherein the SBP comprises: at least 10 consecutive amino acids from any one or more of SEQ ID NOs: 1-112 and 117. Preferably, the SBP can be comprised of at least 10 consecutive amino acids from any one or more of SEQ ID NOs: 1-112 and 117. Other embodiments include compositions, e.g., wherein there are two or more separate SBPs, wherein each individual SBP comprises at least 10 consecutive amino acids from any one of SEQ ID NOs: 1-112 and 117, preferably any one or more of SEQ ID NOs: 1-5. Embodiments include compositions, e.g., wherein there are two or more separate SBPs, wherein the individual SBPs are comprised of one or more of SEQ ID NOs: 1-117.

The invention also provides compositions for delivering a therapeutic or diagnostic agent to a disease site in a mammal comprising a therapeutically or diagnostically effective amount of a pharmaceutical composition comprising the therapeutic or diagnostic agent coupled to a SBP, pharmaceutically acceptable carrier, and a pharmaceutically acceptable carrier, further comprising an albumin binding peptide ("ABP"), wherein the ABP comprises a SEQ ID NO: 119 or SEQ ID NO: 120 or both SEQ ID NOs: 119 and 120. Such compositions include, wherein the SBP and the ABP are in the same polypeptide and wherein the SBP and the ABP are in different polypeptides.

The invention further provides methods for delivering a therapeutic or diagnostic agent to a disease site in a mammal comprising a therapeutically or diagnostically effective amount of a pharmaceutical composition comprising the therapeutic or diagnostic agent coupled to a SPARC-binding-peptide and a pharmaceutically acceptable carrier, ("inventive methods") wherein the SBP comprises SEQ ID Nos: 1-117. Preferred embodiments include inventive methods wherein the compositions, e.g., wherein the SBP comprises: at least 10 consecutive amino acids from any one or more of SEQ ID NOs: 1-112 and 117, more preferably from any one or more of SEQ ID NOs: 1-5 and 117.

Other preferred embodiments include inventive methods, e.g., wherein there are two or more separate SBPs, wherein the individual SBPs are comprised of one or more of SEQ ID NO: 1-117. The invention also provides inventive methods, wherein there are two or more separate polypeptides each comprised of at least one SBP and wherein the SBPs comprise at least 10 consecutive amino acids from any one of SEQ ID NOs: 1-112.

Particularly preferred inventive methods include compositions, e.g., wherein the therapeutic agent is an antibody fragment comprising a functional antibody Fc domain such as wherein the antibody fragment comprises SEQ ID NO: 118. Such methods in accordance with the invention include, e.g., wherein the therapeutic agent is an antibody fragment which mediates one or more of complement activation, cell mediated cytotoxicity, inducing apoptosis, inducing cell death, and opsinization.

The inventive methods provided by the invention also include serum albumin-binding-peptides ("ABPs") comprising SEQ ID NOS: 119 or 120 or both SEQ ID NOS: 119 and 120. Methods in accordance with the invention further include, e.g., both wherein the SBP and the ABP are in the same polypeptide and wherein the SBP and the ABP are in different polypeptides. However, the SBP can also be comprised of at least 10 consecutive amino acids from any one or more of SEQ ID NOS: 1-112.

The inventive compositions and inventive methods provided can be employed wherein the disease site is a tumor and wherein the mammal is a human patient.

BRIEF DESCRIPTION OF THE SEVERAL VIEWS OF THE DRAWING(S)

FIG. 3 depicts the sequences identified after screening a peptide phage display library for binding to SPARC by number of times the sequence is isolated.

FIG. 4 depicts the sequences identified after screening a peptide phage display library for binding to SPARC by the avidity of binding to SPARC (as indicated by OD).

FIG. 6 demonstrates the DNA sequence resulting from the cloning of the sequences encoding peptide 15 and peptide 21 into the pFUSE-hIgG1-Fc2 vector to encode peptide-Fc fusion proteins.

Figure 7:
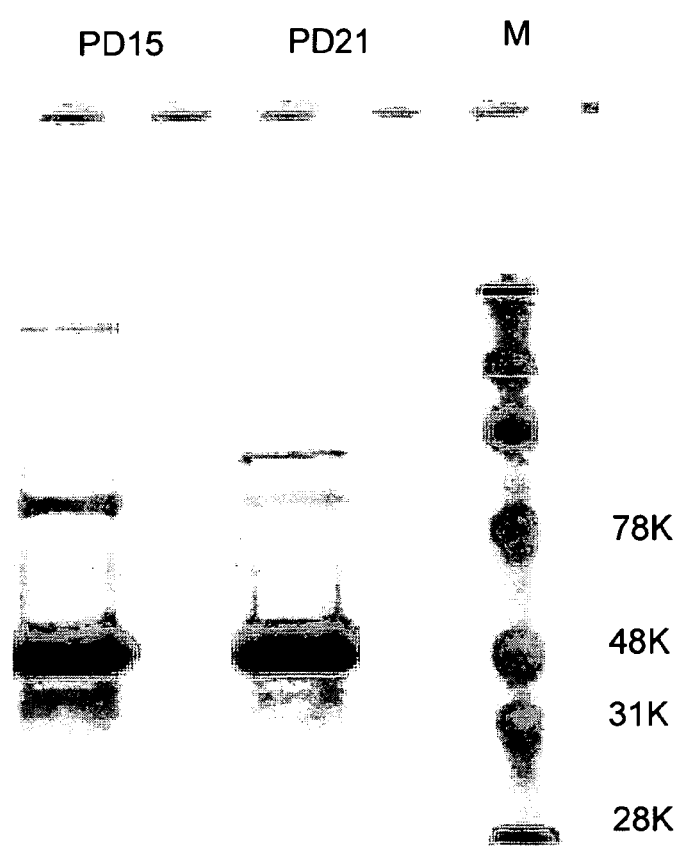

FIG. 7 depicts the expressed and purified PD 15-Fc and PD 21-Fc fusion proteins in polyacrylamide gel electrophoresis.

Figure 8:
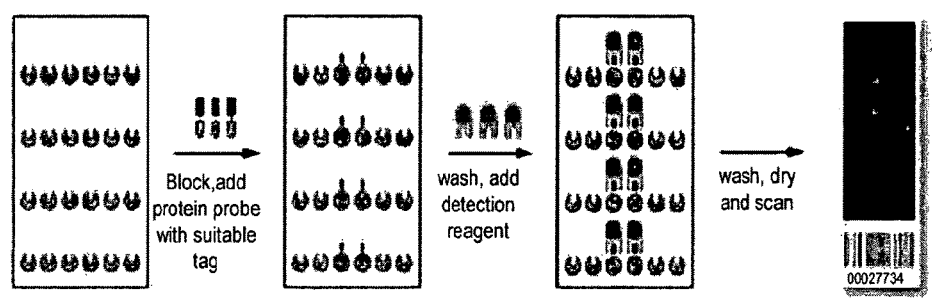

FIG. 8 depicts the Protoarray used to define off target binding of PD15 and PD21.

Figure 9:
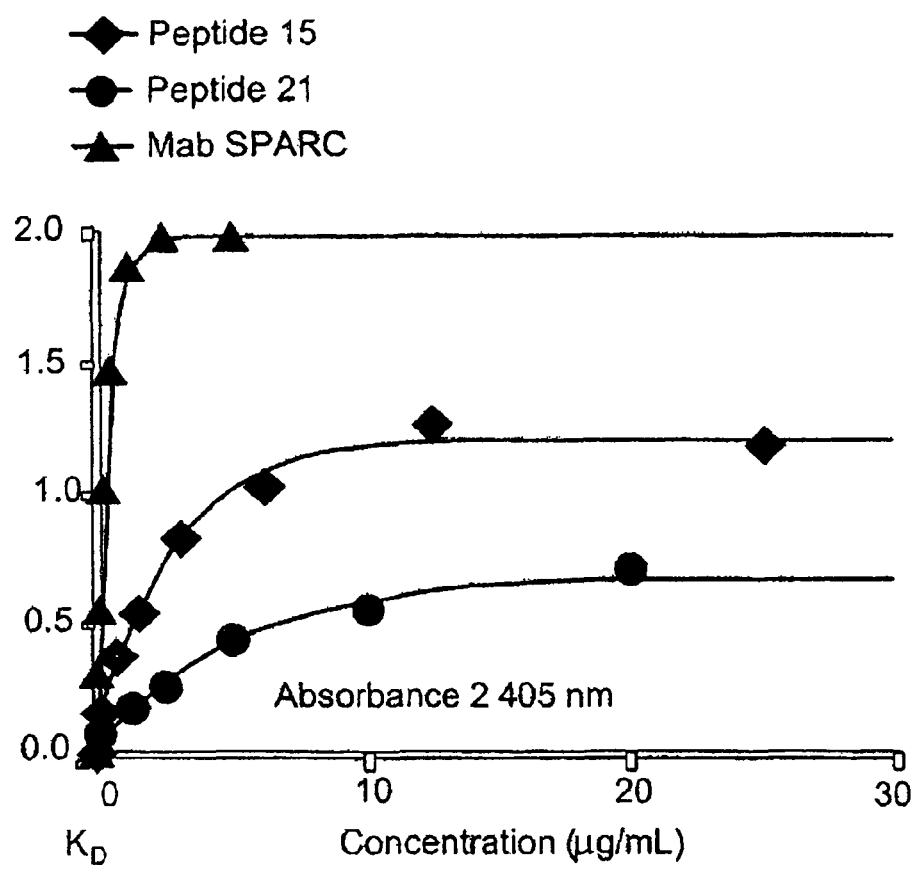

FIG. 9 is a graph of ELISA binding assays comparing the avidity of SPARC binding by PD 15 and PD 21 to that of an anti-SPARC antibody.

Figure 10:
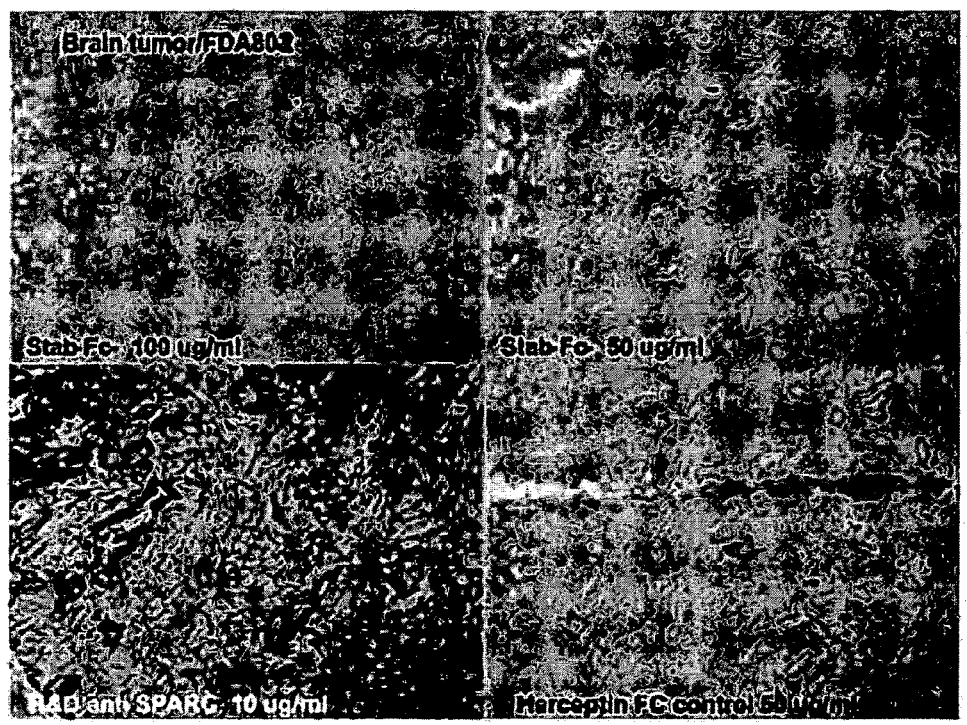

FIG. 10 presents photomicrographs of immunohistolgic studies performed on sections of a human tumor demonstrating tumor SPARC expression with an anti-SPARC antibody (R&D Anti SPARC). The negative control anti-Herceptin antibody (Fc fragment only) and a Stablin binding peptide-Fc fusion protein (stab-Fc) do not stain the tumor.

Figure 11:
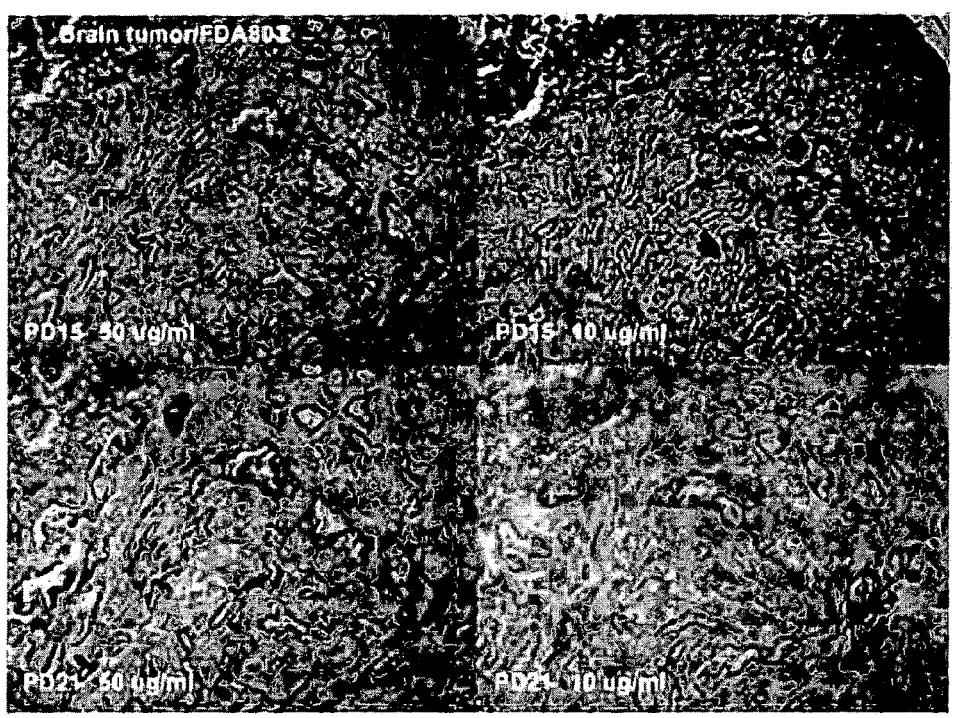

FIG. 11 depicts the histologic staining of a SPARC expressing tumor demonstrating the binding of PD 15 and PD 21 to the SPARC expressing cells of the tumor.

FIG. 12 depicts a potential SPARC binding site on elastin.

Figure 13:
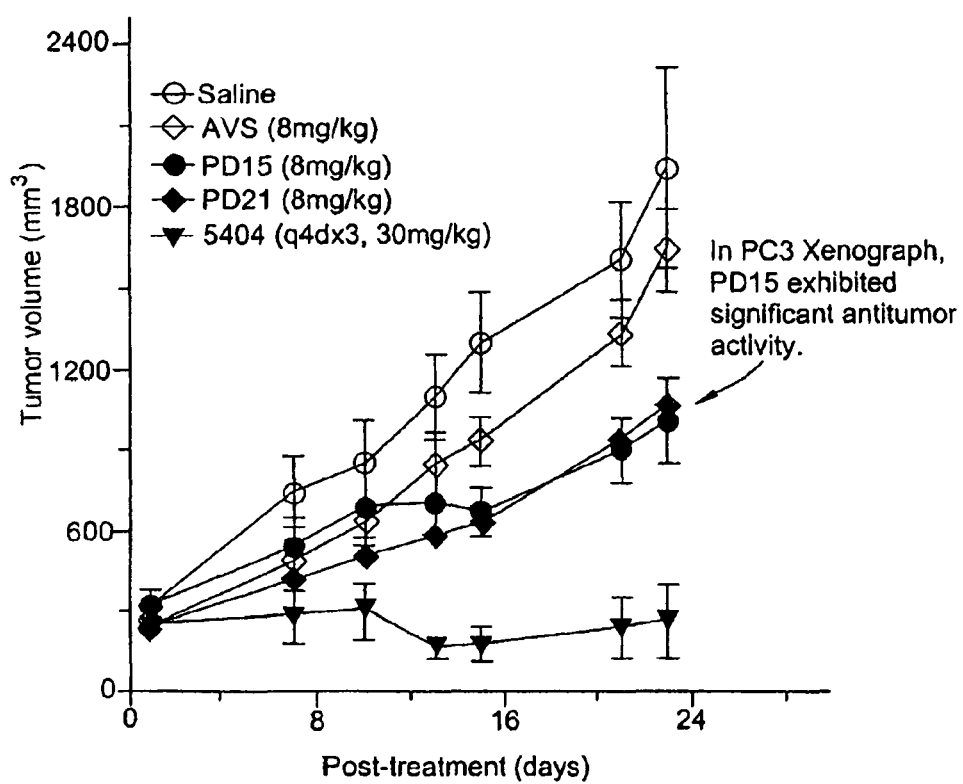

FIG. 13 depicts the antitumor activity of PD 15 and PD 21 in a human prostate cancer/nude mouse model system.

Figure 14:
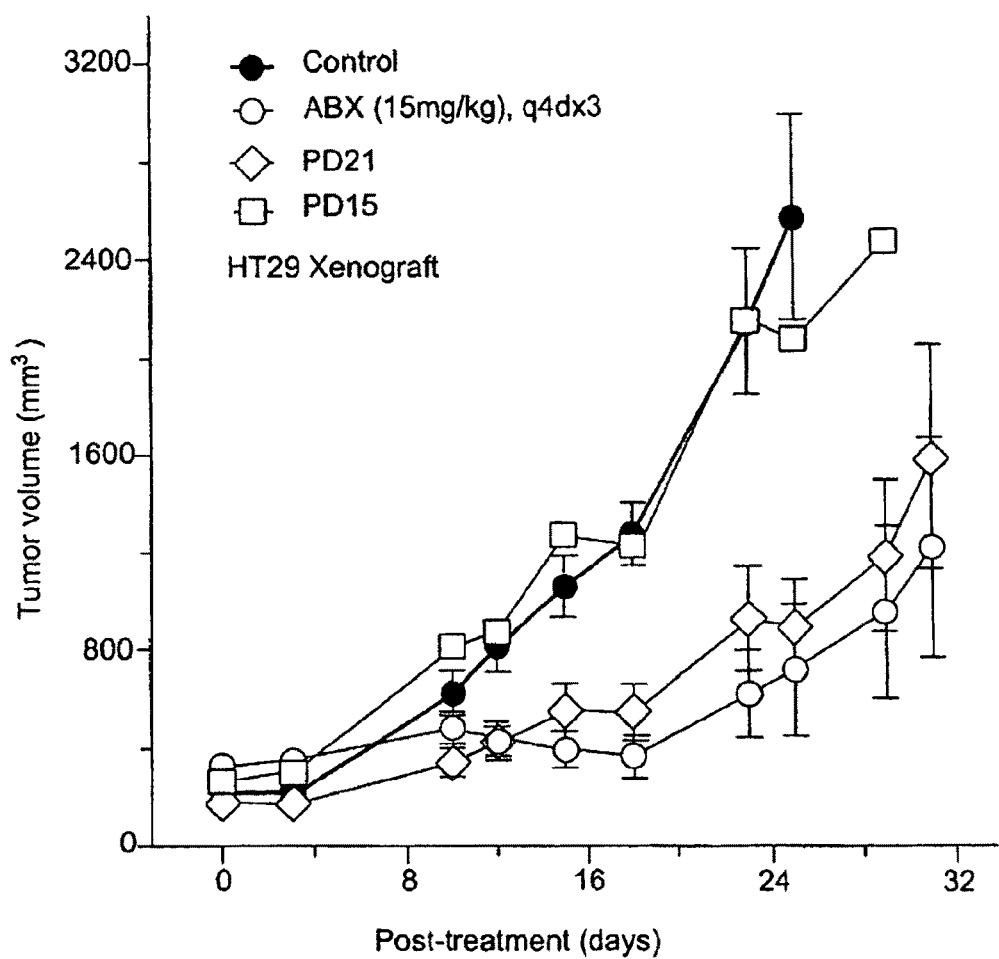

FIG. 14 depicts the antitumor activity of PD15 and PD 21 in a human breast cancer/nude mouse model system.

FIG. 15 depicts two svFc polypeptides, ScFv 3-1 and ScFv 3-2, with SPARC binding activity.

FIG. 16 depicts two svFc polypeptides, ScFv 2-1 and ScFv 2-2, with SPARC binding activity.

FIG. 17 depicts the nucleotide sequence of scfv 2-1, 2-2, 3-1, and 3-2. The CDRs are underlined.

FIG. 18 depicts the purification of scfv2-1 from bacteria.

FIG. 19 depicts the purification of scfv3-1 from bacteria.

Figure 20:
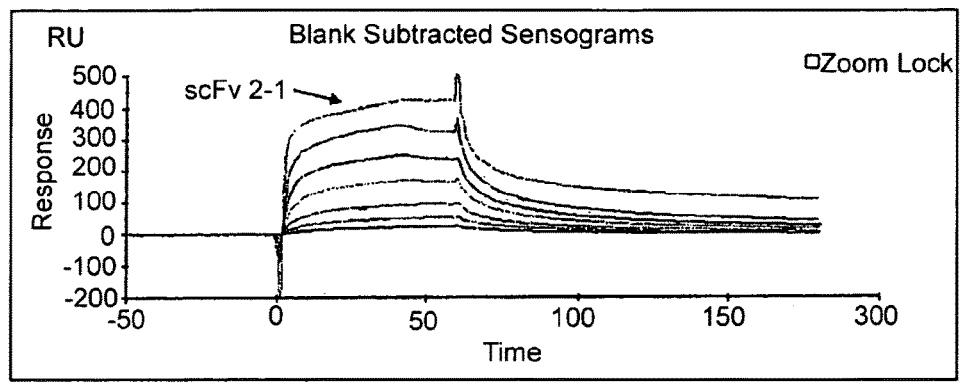

FIG. 20 depicts the binding of scfv2-1 to SPARC immobilized on a chip by Biacore™. The Kds for scfv 2-1, 3-1, and 3-2 for SPARC using Biacore™ are listed (HTI SPARC-purified platelet SPARC obtained from HTI; and Abx SPARC-SPARC from engineered HEK293 cells produced by Abraxis)

DETAILED DESCRIPTION OF THE INVENTION

SBPs and ABPs are "peptide ligand domains." The term "peptide ligand domain" means an amino acid sequence which can exist either by itself and/or within in a larger polypeptide sequence and which binds another biomolecule with specificity. For example, the main blood transport system for fatty acids, bilirubin, tryptophan, calcium, steroid hormones and other physiologically important compounds involves the binding of these biomolecules to serum albumin. The binding of these biomolecules occurs at discrete sites in the albumin amino acid sequences, i.e., at peptide ligand domains in serum albumin.

The invention provides compositions for delivering a therapeutic or diagnostic agent to a disease site in a mammal comprising a therapeutically or diagnostically effective amount of a pharmaceutical composition comprising the therapeutic or diagnostic agent coupled to a SPARC-binding-peptide ("SBP") and a pharmaceutically acceptable carrier ("inventive compositions" and "inventive methods"). The present invention includes compositions and methods wherein the SBP comprises a peptide with the sequence of any one or more of SEQ ID NOs: 1-117, and most desirably, any one or more of SEQ ID NOS: 1-5, or one or more homologs of any one of SEQ ID NOs: 1-117.

The term "homolog" means a polypeptide having substantially the same amino acid sequence as the original sequence and exhibiting relevant properties that are substantially similar to the properties exhibited by the original sequence. Illustrative of one such property is the ability to modulate the tissue distribution of an active agent, wherein a homolog of SEQ ID NOs: 1-117 would be able to provide a substantially similar level of modulation to that provided by SEQ ID NOs: 1-117. In this context, for example and desirably, a homolog of SEQ ID NOs: 1-117 exhibiting such substantially similar modulation would provide a blood level of the active agent of at last about 80%, preferably at least about 85%, more preferably at least about 90%, and most preferably at least about 95%, relative to that provided by SEQ ID NOs: 1-117. Alternatively, the term "homolog" also refers to, e.g., a peptide sequence of at least 6 consecutive amino acids, preferably at least 7 consecutive amino acids, more preferably at least 8 consecutive amino acids, even more preferably at least 9 consecutive amino acids, most preferably at least 10 consecutive amino acids of any one of SEQ ID NOs: 1-112, and most desirably, any one or more of SEQ ID NOs: 1-5.

The compositions and methods provided by the invention also include ABPs comprising SEQ ID NOS: 119 or 120 or both SEQ ID NOS: 119 and 120 and homologs thereof. Methods in accordance with the invention further include, e.g., both wherein the SBP and the ABP are in the same polypeptide and wherein the SBP and the ABP are in different polypeptides.

In the context of changes relative to the original sequence, a homolog of an original sequence will desirably be at least about 80% identical to the original sequence, preferably be at least about 90% identical to the original sequence, even more preferably be at least about 95% identical to the original sequence, and most preferably be at least about 99% identical to the original sequence.

As used herein, "percentage of sequence identity" means the value determined by comparing two optimally aligned sequences over a comparison window. Additionally, the portion of the polypeptide sequence in the comparison window can comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. Preferably, optimal alignment is conducted using the homology alignment algorithm of Needleman and Wunsch (1970) J. Mol. Biol. 48:443 453.

It is also desirable that where the homologs do not contain identical amino acids, the mutations result in only conservative amino acid changes. Accordingly, the residue positions which are not identical differ such that amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity". Means for making this adjustment are well known to those of skill in the art.

In order to further exemplify what is meant by a "conservative" amino acid substitution or change in the context of the present invention, Groups A-F are listed below. The replacement of one member of the following groups by another member of the same group is considered to be a "conservative" substitution.

Group A includes leucine, isoleucine, valine, methionine, phenylalanine, serine, cysteinee, threonine, and modified amino acids having the following side chains: ethyl, isobutyl, —CH2CH2OH, —CH2CH2CH2OH, —CH2CHOHCH3 and CH2SCH3.

Group B includes glycine, alanine, valine, serine, cysteinee, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —(CH2)3COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitrulline, 2-amino guanidinobutanoic acid, homologs of lysine, homologs of arginine, and ornithine.

Group F includes serine, threonine, cysteinee, and modified amino acids having C1-C5 straight or branched alkyl side chains substituted with —OH or —SH.

The invention further provides compositions comprising a conjugate molecule, the conjugate molecule comprising a peptide ligand domain conjugated to an active agent, wherein the peptide ligand domain comprises up to an additional about 50 amino acids, preferably up to an additional about 25 amino acids, more preferably up to an additional about 15 amino acids, and most preferably up to an additional about 10 amino acids added to the amino or carboxyl terminus or both termini. The resulting polypeptides, which are in accordance with the invention, include polypeptides that are less than 50, less than 40, less than 30, less than 25 or less than 20 amino acids in total length.

The invention further provides compositions comprising a conjugate molecule, the conjugate molecule comprising a SBP conjugated to an active agent, wherein there are one or multiple SBP comprising any one of SEQ ID NOs: 1 to-117, and most desirably, any one or more of SEQ ID NOS: 1, 2, and 117.

The invention further provides isolated polynucleotides which encode polypeptides having the amino acid sequence of peptide ligand binding domain including those with said additional amino acid are added to the amino and/or carboxyl termini.

II. Methods of Making Peptides in Accordance with the Invention

The peptide ligand domain-containing polypeptides provided by the present invention can be synthesized, detected, quantified and purified using known technologies. For example, cells expressing exogenous peptide ligand domain-containing polypeptides can be generated by placing a cDNA under the control of strong promoter/translation start and the vector transfected or transformed into suitable prokaryotic or eukaryotic cells to drive the expression of peptide ligand domain-containing polypeptides by methods well known to those of ordinary skill in the art. Alternatively, peptide ligand domain-containing polypeptides can be made chemically by methods well known to those of ordinary skill in the art.

The peptide ligand domain-containing polypeptides can be prepared by standard solid phase synthesis. As is generally known, peptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems, Foster City, Calif., or Biosearch Corporation in San Raphael, Calif.

For example, the peptides are synthesized using standard automated solid-phase synthesis protocols employing t-butoxycarbonyl-alpha-amino acids with appropriate side-chain protection. Completed peptide is removed from the solid phase support with simultaneous side-chain deprotection using the standard hydrogen fluoride method. Crude peptides are further purified by semi-preparative reverse phase-HPLC (Vydac C18) using acetonitrile gradients in 0.1% trifluoroacetic acid (TFA). The peptides are vacuum dried to remove acetonitrile and lyophilized from a solution of 0.1% TFA in water. Purity is verified by analytical RP-HPLC. The peptides can be lyophilized and then solubilized in either water or 0.01M acetic acid at concentrations of 1-2 mg/mL by weight.

The use of the aforementioned synthetic methods is needed if nonencoded amino acids or the D-forms of amino acids occur in the peptides. However, for peptides which are gene-encoded, recourse can also be had through recombinant techniques using readily synthesized DNA sequences in commercially available expression systems.

The invention accordingly provides for a recombinant vector comprising the comprising a elements controlling the expression of a polynucleotide sequence encoding a peptide ligand domain-containing polypeptide. In addition, the invention provides for a cell comprising a nucleic acid encoding a peptide ligand domain-containing polypeptide, wherein the cell is a prokaryotic cell or a eukaryotic cell. Methods of microbial and tissue culture are well known to the skilled artisan (see, e.g., Sambrook & Russell, Molecular Cloning: A Laboratory Manual, Cold Spring Harbor Laboratory Press, New York (2001), pp. 16.1-16.54). The invention thus provides for method of making peptide ligand domain-containing polypeptides comprising: (a) transforming cells with a nucleic acid encoding the polypeptide of claim 1; (b) inducing the expression of the polypeptide by the transformed cells; and (c) purifying the polypeptide.

Protein expression is dependent on the level of RNA transcription, which is in turn regulated by DNA signals. Similarly, translation of mRNA requires, at the very least, an AUG initiation codon, which is usually located within 10 to 100 nucleotides of the 5' end of the message. Sequences flanking the AUG initiator codon have been shown to influence its recognition. For example, for recognition by eukaryotic ribosomes, AUG initiator codons embedded in sequences in conformity to a perfect "Kozak consensus" sequence result in optimal translation (see, e.g., Kozak, J. Molec. Biol. 196: 947-950 (1987)). Also, successful expression of an exogenous nucleic acid in a cell can require post-translational modification of a resultant protein.

The nucleic acid molecules described herein preferably comprise a coding region operatively linked to a suitable promoter, for example, a promoter functional in eukaryotic cells. Viral promoters, such as, without limitation, the RSV promoter and the adenovirus major late promoter can be used in the invention. Suitable non-viral promoters include, but are not limited to, the phosphoglycerokinase (PGK) promoter and the elongation factor 1α promoter. Non-viral promoters are desirably human promoters. Additional suitable genetic elements, many of which are known in the art, also can be attached to, or inserted into the inventive nucleic acid and constructs to provide additional functions, level of expression, or pattern of expression.

In addition, the nucleic acid molecules described herein may be operatively linked to enhancers to facilitate transcription. Enhancers are cis-acting elements of DNA that stimulate the transcription of adjacent genes. Examples of enhancers which confer a high level of transcription on linked genes in a number of different cell types from many species include, without limitation, the enhancers from SV40 and the RSV-LTR. Such enhancers can be combined with other enhancers which have cell type-specific effects, or any enhancer may be used alone.

To optimize protein production in eukaryotic cells, the inventive nucleic acid molecule can further comprise a polyadenylation site following the coding region of the nucleic acid molecule. Also, preferably all the proper transcription signals (and translation signals, where appropriate) will be correctly arranged such that the exogenous nucleic acid will be properly expressed in the cells into which it is introduced. If desired, the exogenous nucleic acid also can incorporate splice sites (i.e., splice acceptor and splice donor sites) to facilitate mRNA production while maintaining an inframe, full length transcript. Moreover, the inventive nucleic acid molecules can further comprise the appropriate sequences for processing, secretion, intracellular localization, and the like.

The nucleic acid molecules can be inserted into any suitable vector. Suitable vectors include, without limitation, viral vectors. Suitable viral vectors include, without limitation, retroviral vectors, alphaviral, vaccinial, adenoviral, adeno associated viral, herpes viral, and fowl pox viral vectors. The vectors preferably have a native or engineered capacity to transform eukaryotic cells, e.g., CHO-K1 cells. Additionally, the vectors useful in the context of the invention can be "naked" nucleic acid vectors (i.e., vectors having little or no proteins, sugars, and/or lipids encapsulating them) such as plasmids or episomes, or the vectors can be complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules.

The nucleic acid molecules described herein can be transformed into any suitable cell, typically a eukaryotic cell, such as, e.g., CHO, HEK293, or BHK, desirably resulting in the expression of a peptide ligand domain-containing polypeptide such as, e.g., polypeptide comprising of SEQ ID NOs: 1-120 or homologs thereof as described herein. The cell can be cultured to provide for the expression of the nucleic acid molecule and, therefore, the production of the peptide ligand domain-containing polypeptide such as, e.g., a polypeptide comprising the amino acid sequence of SEQ ID NOs: 1-120 or homolog thereof as described herein.

Accordingly, the invention provides for a cell transformed or transfected with an inventive nucleic acid molecule described herein. Means of transforming, or transfecting, cells with exogenous DNA molecules are well known in the art. For example, without limitation, a DNA molecule is introduced into a cell using standard transformation or transfection techniques well known in the art such as calcium-phosphate or DEAE-dextran-mediated transfection, protoblast fusion, electroporation, liposomes and direct microinjection (see, e.g., Sambrook & Russell, Molecular Cloning: A Laboratory Manual, Cold Spring Harbor Laboratory Press, New York (2001), pp. 1.1-1.162, 15.1-15.53, 16.1-16.54).

Another example of a transformation method is the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells, and the plasmid DNA is transferred to the nucleus.

Electroporation, the application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest.

Such techniques can be used for both stable and transient transformation of eukaryotic cells. The isolation of stably transformed cells requires the introduction of a selectable marker in conjunction with the transformation with the gene of interest. Such selectable markers include genes which confer resistance to neomycin as well as the HPRT gene in HPRT negative cells. Selection can require prolonged culture in selection media, at least for about 2-7 days, preferable for at least about 1-5 weeks (see, e.g., Sambrook & Russell, Molecular Cloning: A Laboratory Manual, Cold Spring Harbor Laboratory Press, New York (2001), pp. 16.1-16.54).

A peptide ligand domain-containing polypeptide can be expressed and purified from a recombinant host cell. Recombinant host cells may be prokaryotic or eukaryotic, including but not limited to bacteria such as E. coli, fungal cells such as yeast, insect cells including but, not limited to, drosophila and silkworm derived cell lines, and mammalian cells and cell lines. When expressing a peptide ligand domain-containing polypeptide in a cell, e.g., a human cell, whether, in vitro or in vivo, the codons selected for such the polynucleotide encoding the peptide can be optimized for a given cell type (i.e., species). Many techniques for codon optimization are known in the art (see, e.g., Jayaraj et al, Nucleic Acids Res. 33(9):3011-6 (2005); Fuglsang et al., Protein Expr. Purif. 31(2):247-9 (2003); Wu et al., "The Synthetic Gene Designer: a Flexible Web Platform to Explore Sequence Space of Synthetic Genes for Heterologous Expression," csbw, 2005 IEEE Computational Systems Bioinformatics Conference—Workshops (CSBW'05), pp. 258-259 (2005)).

Issues which must be considered for optimal polypeptide expression in prokaryotes include the expression systems used, selection of host strain, mRNA stability, codon bias, inclusion body formation and prevention, fusion protein and site-specific proteolysis, compartment directed secretion. (see Sorensen et al., Journal of Biotechnology 115 (2005) 113-128, which is hereby incorporated by reference).

Expression is normally induced from a plasmid harboured by a system compatible genetic background. The genetic elements of the expression plasmid include origin of replication (ori), an antibiotic resistance marker, transcriptional promoters, translation initiation regions (TIRs) as well as transcriptional and translational terminators.

Any suitable expression system can be used, for example, Escherichia coli facilitates protein expression by its relative simplicity, high-density cultivation, the well-known genetics and the large number of compatible tools, including a variety of available plasmids, recombinant fusion partners and mutant strains, that are available for polypeptide expression. The E coli strain or genetic background for recombinant expression is highly important. Expression strains should be deficient in the most harmful natural proteases, maintain the expression plasmid stably and confer the genetic elements relevant to the expression system (e.g., DE3).

Plasmid copy number is controlled by the origin of replication that preferably replicates in a relaxed fashion (Baneyx, 1999). The ColE1 replicon present in modern expression plasmids is derived from the pBR322 (copy number 15-20) or the pUC (copy number 500-700) family of plasmids, whereas the p15A replicon is derived from pACYC184 (copy number 10-12). The most common drug resistance markers in recombinant expression plasmids confer resistance to ampicillin, kanamycin, chloramphenicol or tetracycline.

E coli expression systems include T7 based pET expression system (commercialized by Novagen), lambda PL promoter/cI repressor (e.g., Invitrogen pLEX), Trc promoter (e.g., Amersham Biosciences pTrc), Tac promoter (e.g., Amersham Biosciences pGEX) and hybrid lac/T5 (e.g., Qiagen pQE) and the BAD promoter (e.g., Invitrogen pBAD).

Translation initiation from the translation initiation region (TIR) of the transcribed messenger RNA require a ribosomal binding site (RBS) including the Shine-Dalgarno (SD) sequence and a translation initiation codon. The Shine-Dalgarno sequence is located 7±2 nucleotides upstream from the initiation codon, which is the canonical AUG in efficient recombinant expression systems. Optimal translation initiation is obtained from mRNAs with the SD sequence UAAGGAGG.

Codon usage in E. coli is reflected by the level of cognate amino-acylated tRNAs available in the cytoplasm. Major codons occur in highly expressed genes whereas the minor or rare codons tend to be in genes expressed at low levels. Codons rare in E. coli are often abundant in heterologous genes from sources such as eukaryotes, archaeabacteria and other distantly related organisms with different codon frequency preferencies (Kane, 1995). Expression of genes containing rare codons can lead to translational errors, as a result of ribosomal stalling at positions requiring incorporation of amino acids coupled to minor codon tRNAs (McNulty et al., 2003). Codon bias problems become highly prevalent in recombinant expression systems, when transcripts containing rare codons in clusters, such as doublets and triplets accumulate in large quantities.

Protein activity demands folding into precise three dimensional structures. Stress situations such as heat shock impair folding in vivo and folding intermediates tend to associate into amorphous protein granules termed inclusion bodies.

Inclusion bodies are a set of structurally complex aggregates often perceived to occur as a stress response when recombinant protein is expressed at high rates. Macromolecular crowding of proteins at concentrations of 200-300 mg/ml in the cytoplasm of E. coli, suggest a highly unfavorable protein-folding environment, especially during recombinant high-level expression (van den Berg et al., 1999). Whether inclusion bodies form through a passive event occurring by hydrophobic interaction between exposed patches on unfolded chains or by specific clustering mechanisms is unknown (Villaverde and Carrio, 2003). The purified aggregates can be solubilized using detergents like urea and guadinium hydrochloride. Native protein can be prepared by in vitro refolding from solubilized inclusion bodies either by dilution, dialysis or on-column refolding methods (Middelberg, 2002; Sørensen et al., 2003a).

Refolding strategies might be improved by inclusion of molecular chaperones (Mogk et al., 2002). Optimization of the refolding procedure for a given protein however require time consuming efforts and is not always conducive to high product yields. A possible strategy for the prevention of inclusion body formation is the co-overexpression of molecular chaperones.

A wide range of protein fusion partners has been developed in order to simplify the purification and expression of recombinant proteins (Stevens, 2000). Fusion proteins or chimeric proteins usually include a partner or "tag" linked to the passenger or target protein by a recognition site for a specific protease. Most fusion partners are exploited for specific affinity purification strategies. Fusion partners are also advantageous in vivo, where they might protect passengers from intracellular proteolysis (Jacquet et al., 1999; Martinez et al., 1995), enhance solubility (Davis et al., 1999; Kapust and Waugh, 1999; Sorensen et al., 2003b) or be used as specific expression reporters (Waldo et al., 1999). High expression levels can often be transferred from a N-terminal fusion partner, to a poorly expressing passenger, most probably as a result of mRNA stabilization (Arechaga et al., 2003). Common affinity tags are the polyhistidine tag (His-tag), which is compatible with immobilized metal affinity chromatography (IMAC) and the glutathione S-transferase (GST) tag for purification on glutathione based resins. Several other affinity tags exist and have been extensively reviewed (Terpe, 2003).

Recombinantly expressed proteins can in principle be directed to three different locations namely the cytoplasm, the periplasm or the cultivation medium. Various advantages and disadvantages are related to the direction of a recombinant protein to a specific cellular compartment. Expression in the cytoplasm is normally preferable since production yields are high. Disulfide bond formation is segregated in *E. coli* and is actively catalyzed in the periplasm by the Dsb system (Rietsch and Beckwith, 1998). Reduction of cysteines in the cytoplasm is achieved by thioredoxin and glutaredoxin. Thioredoxin is kept reduced by thioredoxin reductase and glutaredoxin by glutathione. The low molecular weight glutathione molecule is reduced by glutathione reductase. Disruption of the trxB and gor genes encoding the two reductases, allow the formation of disulfide bonds in the *E. coli* cytoplasm.

Cell-based expression systems have drawbacks in terms of the quality and quantity of the proteins produced and are not always appropriate for high-throughput production. Many of these shortcomings can be circumvented by the use of cell-free translation systems.

Cell-free systems for in vitro gene expression and protein synthesis have been described for many different prokaryotic and eukaryotic systems (see Endo & Sawasaki Current Opinion in Biotechnology 2006, 17:373-380. Eukaryotic cell-free systems, such as rabbit reticulocyte lysate and wheat germ extract, are prepared from crude extract containing all the components required for translation of in vitro-transcribed RNA templates. Eukaryotic cell-free systems use isolated RNA synthesized in vivo or in vitro as a template for the translation reaction (e.g., Rabbit Reticulocyte Lysate Systems or Wheat Germ Extract Systems). Coupled eukaryotic cell-free systems combine a prokaryotic phage RNA polymerase with eukaryotic extracts and utilize an exogenous DNA or PCR-generated templates with a phage promoter for in vitro protein synthesis (e.g., TNT® Coupled Reticulocyte Lysate Proteins translated using the TNT® Coupled Systems can be used in many types of functional studies. TNT® Coupled Transcription/Translation reactions have traditionally been used to confirm open reading frames, study protein mutations and make proteins in vitro for protein-DNA binding studies, protein activity assays, or protein-protein interaction studies. Recently, proteins expressed using the TNT® Coupled Systems have also been used in assays to confirm yeast two-hybrid interactions, perform in vitro expression cloning (IVEC) and make protein substrates for enzyme activity or protein modification assays. For a listing of recent citations using the TNT® Coupled Systems in various applications, please visit: www.promega.com/citations/

Transcription and translation are typically coupled in prokaryotic systems; that is, they contain an endogenous or phage RNA polymerase, which transcribes mRNA from an exogenous DNA template. This RNA is then used as a template for translation. The DNA template may be either a gene cloned into a plasmid vector (cDNA) or a PCR(a)-generated template. A ribosome binding site (RBS) is required for templates translated in prokaryotic systems. During transcription, the 5'-end of the mRNA becomes available for ribosome binding and translation initiation, allowing transcription and translation to occur simultaneously. Prokaryotic systems are available that use DNA templates containing either prokaryotic promoters (such as lac or tac; *E. coli* S30 Extract System for Circular and Linear DNA or a phage RNA polymerase promoter; *E. coli* T7 S30 Extract System for Circular DNA Solubility of a purified peptide ligand domain-containing polypeptide can be improved by methods known in the art. For example, to increase the solubility of an expressed protein (e.g., in *E. coli*), one can reduce the rate of protein synthesis by lowering the growth temperature, using a weaker promoter, using a lower copy number plasmid, lowering the inducer concentration, changing the growth medium as described in Georgiou & Valax (Current Opinion Biotechnol. 7:190-197 (1996)). This decreases the rate of protein synthesis and usually more soluble protein is obtained. One can also add prosthetic groups or cofactors which are essential for proper folding or for protein stability, or add buffer to control pH fluctuation in the medium during growth, or add 1% glucose to repress induction of the lac promoter by lactose, which is present in most rich media (such as LB, 2xYT). Polyols (e.g., sorbitol) and sucrose may also be added to the media because the increase in osmotic pressure caused by these additions leads to the accumulation of osmoprotectants in the cell, which stabilize the native protein structure. Ethanol, low molecular weight thiols and disulfides, and NaCl may be added. In addition, chaperones and/or foldases may be co-expressed with the desired polypeptide. Molecular chaperones promote the proper isomerization and cellular targeting by transiently interacting with folding intermediates. *E. coli* chaperone systems include but, are not limited to: GroES-GroEL, DnaK-DnaJ-GrpE, ClpB.

Foldases accelerate rate-limiting steps along the folding pathway. Three types of foldases play an important role: peptidyl prolyl cis/trans isomerases (PPI's), disulfide oxidoreductase (DsbA) and disulfide isomerase (DsbC), protein disulfide isomerase (PDI) which is an eukaryotic protein that catalyzes both protein cysteine oxidation and disulfide bond isomerization. Co-expression of one or more of these proteins with the target protein could lead to higher levels of soluble target protein.

A peptide ligand domain-containing polypeptide can be produced as a fusion protein in order to improve its solubility and production. The fusion protein comprises a peptide ligand domain-containing polypeptide and a second polypeptide fused together in frame. The second polypeptide may be a fusion partner known in the art to improve the solubility of the polypeptide to which it is fused, for example, NusA, bacterioferritin (BFR), GrpE, thioredoxin (TRX) and glutathione-S-transferase (GST). Novagen Inc. (Madison, Wis.) provides the pET 43.1 vector series which permit the formation of a NusA-target fusion. DsbA and DsbC have also shown positive effects on expression levels when used as a fusion partner, therefore can be used to fuse with a peptide ligand domain for achieving higher solubility.

In an aspect of such fusion proteins, the expressed peptide ligand domain-containing polypeptide includes a linker polypeptide comprises a protease cleavage site comprising a peptide bond which is hydrolyzable by a protease. As a result, the peptide ligand domain in a polypeptide can be separated from the remainder of the polypeptide after expression by proteolysis. The linker can comprise one or more additional amino acids on either side of the bond to which the catalytic site of the protease also binds (see, e.g., Schecter & Berger, Biochem. Biophys. Res. Commun. 27, 157-62 (1967)). Alternatively, the cleavage site of the linker can be separate from the recognition site of the protease and the two cleavage site and recognition site can be separated by one or more (e.g., two to four) amino acids. In one aspect, the linker comprises at least about 2, 3, 4, 5, 6, 7, 8, 9, about 10, about 20, about 30, about 40, about 50 or more amino acids. More preferably the linker is from about 5 to about 25 amino acids in length, and most preferably, the linker is from about 8 to about 15 amino acids in length.

Some proteases useful according to the invention are discussed in the following references: Hooper et al., Biochem. J. 321: 265-279 (1997); Werb, Cell 91: 439-442 (1997); Wolfsberg et al., J. Cell Biol. 131: 275-278 (1995); Murakami & Etlinger, Biochem. Biophys. Res. Comm. 146: 1249-1259 (1987); Berg et al., Biochem. J. 307: 313-326 (1995); Smyth and Trapani, Immunology Today 16: 202-206 (1995); Talanian et al., J. Biol. Chem. 272: 9677-9682 (1997); and Thornberry et al., J. Biol. Chem. 272: 17907-17911 (1997). Cell surface proteases also can be used with cleavable linkers according to the invention and include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; Urokinase plasminogen activator; Tissue plasminogen activator; Plasmin; Thrombin; BMP-1 (procollagen C-peptidase); ADAM 1, 2, 3, 4, 5, 6, 7, 8, 9, 10, and 11; and, Granzymes A, B, C, D, E, F, G, and H.

An alternative to relying on cell-associated proteases is to use a self-cleaving linker. For example, the foot and mouth disease virus (FMDV) 2A protease may be used as a linker. This is a short polypeptide of 17 amino acids that cleaves the polyprotein of FMDV at the 2A/2B junction. The sequence of the FMDV 2A propeptide is NFDLLKLAGDVESNPGP. Cleavage occurs at the C-terminus of the peptide at the final glycine-proline amino acid pair and is independent of the presence of other FMDV sequences and cleaves even in the presence of heterologous sequences.

Affinity chromatography can be used alone or in conjunction with ion-exchange, molecular sizing, or HPLC chromatographic techniques in the purification of peptide ligand domain-containing polypeptides. Such chromatographic approach can be performed using columns or in batch formats. Such chromatographic purification methods are well known in the art.

Additionally, the invention provides for isolated nucleic acids encoding peptide ligand domain-containing polypeptides with one or more amino acid substitutions and insertions or deletions of from about 1 to about 5 amino acids, preferably from about 1 to about 3 amino acids, more preferably 1 amino acid, in the SEQ ID NOs: 1-117 sequences, wherein the relevant properties that are substantially similar to the properties exhibited by the original sequence.

Mutagenesis can be undertaken by any of several methods known in the art. Generally, mutagenesis can be accomplished by cloning the nucleic acid sequence into a plasmid or some other vector for ease of manipulation of the sequence. Then, a unique restriction site at which further nucleic acids can be added into the nucleic acid sequence is identified or inserted into the nucleic acid sequence. A double-stranded synthetic oligonucleotide generally is created from overlapping synthetic single-stranded sense and antisense oligonucleotides such that the double-stranded oligonucleotide incorporates the restriction sites flanking the target sequence and, for instance, can be used to incorporate replacement DNA. The plasmid or other vector is cleaved with the restriction enzyme, and the oligonucleotide sequence having compatible cohesive ends is ligated into the plasmid or other vector to replace the original DNA.

Other means of in vitro site-directed mutagenesis are known to those skilled in the art, and can be accomplished (in particular, using an overlap-extension polymerase chain reaction (PCR), see, e.g., Parikh & Guengerich, Biotechniques 24:428-431 (1998)). Complementary primers overlapping the site of change can be used to PCR amplify the whole plasmid in a mixture containing 500 mM dNTPs, 2 units of Pfu polymerase, 250 ng each of sense and antisense primers, and 200 ng of plasmid DNA comprising a sequence encoding Peptide ligand domain-containing polypeptide. The PCR desirably involves 18 cycles with an extension time of 2.5 minutes for each Kb of DNA. The PCR products can be treated with DpnI (which only digests the adenine-methylated plasmid DNA) and transformed into *Escherichia coli* DH5α cells. Transformants can be screened by restriction enzyme digestion for incorporation of the changes, which then can be confirmed by DNA sequence analysis.

Suitable methods of protein detection and quantification of peptide ligand domain-containing polypeptides include Western blot, enzyme-linked immunosorbent assay (ELISA), silver staining, the BCA assay (see, e.g., Smith et al., Anal. Biochem., 150, 76-85 (1985)), the Lowry protein assay (described in, e.g., Lowry et al., J. Biol. Chem., 193, 265-275 (1951)) which is a colorimetric assay based on protein-copper complexes, and the Bradford protein assay (described in, e.g., Bradford et al., Anal. Biochem., 72, 248 (1976)) which depends upon the change in absorbance in Coomassie Blue G-250 upon protein binding. Once expressed, the peptide ligand domain-containing polypeptides can be purified by traditional purification methods such as ionic exchange, size exclusion, or C18 chromatography.

III. Methods of Coupling Peptide Ligand Domains

Methods for "coupling" (or "conjugation" or "cross-linking") of suitable active agents such as, e.g., therapeutics, chemotherapeutics, radionuclides, polypeptides, and the like, to peptide ligand domain-containing polypeptide are well described in the art. In preparing the conjugates provided herein, the active agent is linked either directly or indirectly peptide ligand domain by any method presently known in the art for attaching two moieties, so long as the attachment of the conjugating or coupling moiety to the peptide ligand domain does not substantially impede its function of the peptide ligand domain or substantially impede the function of the active agent. The coupling can be by any suitable means, including, but are not limited to, ionic and covalent bonds, and any other sufficiently stable association, whereby the targeted agent's distribution will be modulated.

Numerous heterobifunctional cross-linking reagents that are used to form covalent bonds between amino groups and thiol groups and to introduce thiol groups into proteins, are known to those of skill in this art (see, e.g., Cumber et al. (1992) Bioconjugate Chem. 3':397 401; Thorpe et al. (1987) Cancer Res. 47:5924 5931; Gordon et al. (1987) Proc. Natl. Acad. Sci. 84:308 312; Walden et al. (1986) J. Mol. Cell Immunol. 2:191 197; Carlsson et al. (1978) Biochem. J. 173: 723 737; Mahan et al. (1987) Anal. Biochem. 162:163 170; Wawryznaczak et al. (1992) Br. J. Cancer 66:361 366;

Fattom et al. (1992) Infection & Immun. 60:584 589). These reagents may be used to form covalent bonds between a peptide ligand domain or a peptide ligand domain-containing polypeptide and any of the active agents disclosed herein. These reagents include, but are not limited to: N-succinimidyl-3-(2-pyridyidithio)propionate (SPDP; disulfide linker); sulfosuccinimidyl 6-[3-(2-pyridyldithio)propionamido]hexanoate (sulfo-LC-SPDP); succinimidyloxycarbonyl-α-methyl benzyl thiosulfate (SMBT, hindered disulfate linker); succinimidyl 6-[3-(2-pyridyidithio)propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3-dithiopropionate (SAED); sulfo-succinimidyl 7-azido-4-methylcoumarin-3-acetate (SAMCA); sulfosuccinimidyl 6-[alpha-methyl-alpha-(2-pyridyidithio)toluamido]hexanoate (sulfo-LC-SMPT); 1,4-di-[3'-(2'-pyridyidithio)propionamido]butane (DPDPB); 4-succinimidyloxycarbonyl-α-methyl-α.-(2-pyridylthio)-toluene (SMPT, hindered disulfate linker); sulfosuccinimidyl6[α.-methyl-α.-(2-pyridyldithio)toluamido] hexa-noate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl)amino benzoate (sulfo-SIAB); succinimidyl4(p-maleimidophenyl)butyrate (SMPB); sulfosuccinimidyl-4-(p-maleimidophenyl) butyrate (sulfo-SMPB); azidobenzoyl hydrazide (ABH).

Other heterobifunctional cleavable coupling agents include, N-succinimidyl (4-iodoacetyl)-aminobenzoate; sulfosuccinimydil (4-iodoacetyl)-aminobenzoate; 4-succinimidyl-oxycarbonyl-a-(2-pyridyldithio)-toluene; sulfosuccinimidyl-6-[a-methyl-a-(pyridyldithiol)-toluamido]hexanoate; N-succinimidyl-3-(−2-pyridyidithio)-proprionate; succinimidyl 6[3(−(−2-pyridyldithio)-proprionamido]hexanoate; sulfosuccinimidyl 6[3 (−(−2-pyridyldithio)-propionamido] hexanoate; 3-(2-pyridyidithio)-propionyl hydrazide, Ellman's reagent, dichlorotriazinic acid, S-(2-thiopyridyl)-L-cysteine. Further exemplary bifunctional linking compounds are disclosed in U.S. Pat. Nos. 5,349,066, 5,618,528, 4,569, 789, 4,952,394, and 5,137,877.

Alternatively, e.g., polypeptide suflhydryl groups can be used for conjugation. In addition, sugar moieties bound to glycoproteins, e.g., antibodies can be oxidized to form aldehydes groups useful in a number of coupling procedures known in the art. The conjugates formed in accordance with the invention can be stable in vivo or labile, such as enzymatically degradeable tetrapeptide linkages or acid-labile cis-aconityl or hydrazone linkages.

The peptide ligand domain-containing polypeptide is optionally linked to the active agent via one or more linkers. The linker moiety is selected depending upon the properties desired. For example, the length of the linker moiety can be chosen to optimize the kinetics and specificity of ligand binding, including any conformational changes induced by binding of the ligand to a target receptor. The linker moiety should be long enough and flexible enough to allow the polypeptide ligand moiety and the target cell receptor to freely interact. If the linker is too short or too stiff, there may be steric hindrance between the polypeptide ligand moiety and the cell toxin. If the linker moiety is too long, the active agent may be degraded in the process of production, or may not deliver its desired effect to the target cell effectively.

Any suitable linker known to those of skill in the art can be used herein. Generally a different set of linkers will be used in conjugates that are fusion proteins from linkers in chemically-produced conjugates. Linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers. In some embodiments, several linkers may be included in order to take advantage of desired properties of each linker. Chemical linkers and peptide linkers may be inserted by covalently coupling the linker to the peptide ligand domain-containing polypeptide and the targeted agent. The heterobifunctional agents, described below, may be used to effect such covalent coupling. Peptide linkers may also be linked by expressing DNA encoding the linker and peptide ligand domain, linker and active agent, or peptide ligand domain, linker and active agent as a fusion protein. Flexible linkers and linkers that increase solubility of the conjugates are contemplated for use, either alone or with other linkers are also contemplated herein.

Accordingly, linkers can include, but are not limited to, peptidic linkages, amino acid and peptide linkages, typically containing between one and about 30 amino acids, more preferably between about 10 and 30 amino acids. Alternatively, chemical linkers, such as heterobifunctional cleavable cross-linkers, including but not limited to, N-succinimidyl (4-iodoacetyl)-aminobenzoate, sulfosuccinimydil (4-iodoacetyl)-aminobenzoate, 4-succinimidyl-oxycarbonyl-a-(2-pyridyidithio)toluene, sulfosuccinimidyl-6-a-methyl-a-(pyridyldithiol)-toluamido)hexanoate, N-succinimidyl-3-(−2-pyridyldithio)-proprionate, succinimidyl 6(3(−(−2-pyridyldithio)-proprionamido)hexanoate, sulfosuccinimidyl 6(3 (−(−2-pyridyidithio)-propionamido) hexanoate, 3-(2-pyridyldithio)-propionyl hydrazide, Ellman's reagent, dichlorotriazinic acid, and S-(2-thiopyridyl)-L-cysteine.

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent will be released allows selection of a linker based on the known physiological differences between tissues in need of delivery of a therapeutic agent (see, e.g., U.S. Pat. No. 5,612,474). For example, the acidity of tumor tissues appears to be lower than that of normal tissues.

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) Infection & Immun. 60:584 589) and acid labile transferrin conjugates that contain a sufficient portion of transferrin to permit entry into the intracellular transferrin cycling pathway (see, e.g., Welhoner et al. (1991) J. Biol. Chem. 266:4309 4314). Photocleavable linkers are linkers that are cleaved upon exposure to light (see, e.g., Goldmacher et al. (1992) Bioconj. Chem. 3:104 107, which linkers are herein incorporated by reference), thereby releasing the targeted agent upon exposure to light. Photocleavable linkers that are cleaved upon exposure to light are known (see, e.g., Hazum et al. (1981) in Pept., Proc. Eur. Pept. Symp., 16th, Brunfeldt, K (Ed), pp. 105 110, which describes the use of a nitrobenzyl group as a photocleavable protective group for cysteine; Yen et al. (1989) Makromol. Chem 190:69 82, which describes water soluble photocleavable copolymers, including hydroxypropylmethacrylamide copolymer, glycine copolymer, fluorescein copolymer and methylrhodamine copolymer; Goldmacher et al. (1992) Bioconj. Chem. 3:104 107, which describes a cross-linker and reagent that undergoes photolytic degradation upon exposure to near UV light (350 nm); and Senter et al. (1985) Photochem. Photobiol 42:231 237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

IV. The Invention Provides a Plurality of Active Agents

The various aspects of the present invention contemplate that the peptide ligand domain-containing polypeptide is coupled to an active agent, i.e., a therapeutic or diagnostic agent.

As used herein, the term "therapeutic agent" refers to a chemical compound, a biological macromolecule, or an extract made from biological materials such as bacteria, plants, fungi, or animal (particularly mammalian) cells or tissues that are suspected of having therapeutic properties, e.g., chemotherapeutic agent or radiotherapy agent. The term "therapeutic" as used herein refers to ameliorating the effects of, curing or preventing (illustrated by the prevention or lessening the chance of a targeted disease, e.g., cancer or other proliferative disease) a disease or related condition afflicting a subject mammal. Curative therapy refers alleviating, in whole or in part, an existing disease or condition in a mammal.

The agent can be purified, substantially purified or partially purified. Further, such a therapeutic agent can be in or associated with a liposome or immunoliposome and the conjugation can be directly to the agent or to the liposome/immunoliposome. A 'liposome" is a small vesicle composed of various types of lipids, phospholipids and/or surfactant which is useful for delivery of a drug (e.g., drugs, antibodies, toxins). The components of the liposome are commonly arranged in a bilayer formation, similar to the lipid arrangement of biological membranes.

Illustrative of the therapeutic agents which can be coupled to the peptide ligand domain-containing polypeptide in the manner contemplated by the present invention include, without limitation, chemotherapeutic agents (e.g., docetaxel, paclitaxel, taxanes and platinum compounds), antifolates, antimetabolites, antimitotics, DNA damaging agents, proapoptotics, differentiation inducing agents, antiangiogenic agents, antibiotics, hormones, peptides, antibodies, tyrosine kinase inhibitors, biologically active agents, biological molecules, radionuclides, adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, Taxol® (paelitaxel), combretastatins, discodermolides, transplatinum, tyrosine kinase inhibitors (genistein), and other chemotherapeutic agents.

As used herein, the term "chemotherapeutic agent" refers to an agent with activity against cancer, neoplastic, and/or proliferative diseases. Preferred chemotherapeutic agents include docetaxel and paclitaxel as particles comprising albumin wherein more than 50% of the chemotherapeutic agent is in nanoparticle form. Most preferably, the chemotherapeutic agent comprises particles of albumin-bound paclitaxel, e.g., Abraxane®.

Suitable therapeutic agents also include, e.g., biologically active agents (TNF, of tTF), radionuclides (131I, 90Y, 111In, 211At, 32P and other known therapeutic radionuclides), antiangiogenesis agents (angiogenesis inhibitors, e.g., INF-alpha, fumagillin, angiostatin, endostatin, thalidomide, and the like), other biologically active polypeptides, therapy sensitizers, antibodies, lectins, and toxins.

Suitable diseases for the application of the invention include malignant and premalignant conditions, as well as proliferative disease, including but, not limited to, where the proliferative diseases is, e.g., benign prostatic hyperplasia, endometriosis, endometrial hyperplasia, atherosclerosis, psoriasis, an immunologic proliferation or a proliferative renal glomerulopathy.

The term "therapeutically effective amount" it is meant an amount that returns to normal, either partially or completely, physiological or biochemical parameters associated with or causative of a disease or condition. A clinician skilled in the art should be able to determine amount of the pharmaceutical composition that will be therapeutically effective relative to a particular disease or condition. By way of example, and in accordance with a preferred embodiment wherein the therapeutic agent is paclitaxel, the paclitaxel dose administered can range from about 30 mg/m$^2$ to about 1000 mg/m$^2$ with a dosing cycle of about 3 weeks (i.e., administration of the paclitaxel dose once every about three weeks), desirably from about 50 mg/m$^2$ to about 800 mg/m$^2$, preferably from about 80 mg/m$^2$ to about 700 mg/m$^2$, and most preferably from about 250 mg/m$^2$ to about 300 mg/m$^2$ with a dosing cycle of about 3 weeks, preferably a cycle of about 2 weeks, more preferably weekly cycles.

The present invention also has diagnostic aspects. For example, the diagnostic agent can be a tracer or label, including, without limitation, radioactive agents, MRI contrast agents, X-ray contrast agents, ultrasound contrast agents, and PET contrast agents. The coupling of these agents, described in connection with therapeutic agents, is also contemplated by this aspect of the invention. Further, the term "diagnostically effective amount" is an amount of the pharmaceutical composition that in relevant clinical settings allows for a reasonably accurate determination of the presence and/or extent of abnormal proliferative, hyperplastic, remodeling, inflammatory activity in tissues and organs. For example, the condition "diagnosed" in accordance with the invention can be a benign or malignant tumor.

The diagnostic agents taught herein include polypeptides, such as antibodies, which can be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) Proc. Nat'l Acad. Sci. USA 86:10029-10033.

The delivery of therapeutic or diagnostic agents to a tumor or other disease site by inventive compositions and methods can be monitored and measured by any suitable method including, e.g., adding a radioactive label or radio-opaque label to the composition and imaging as is appropriate and well known to those of ordinary skill in the art. The sequesteration of compositions in the plasma compartment can be monitored by any suitable method including, e.g., venupuncture.

Further, and in a related aspect, the invention provides a method of predicting or determining a tumor's response to a chemotherapeutic agent, as well as a method of predicting or determining a proliferative disease's response to a chemotherapeutic agent or treating a proliferative disease, including but, not limited to, where the proliferative diseases is, e.g., benign prostatic hyperplasia, endometriosis, endometrial hyperplasia, atherosclerosis, psoriasis, immunologic proliferation or a proliferative renal glomerulopathy.

V. The Invention Provides Fusion Proteins which Couple Peptide Ligand Domains to Polypeptide Active Agents The present invention further contemplates the coupling of peptide ligand domains to polypeptide active agents in fusion proteins. For example, and without limitation, peptide ligand domain sequences can be fused upstream or downstream of diagnostically useful protein domains (such as hapten, GFP), a therapy sensitizer, active protein domains, or toxins. Active protein domains may include, without limitation. Truncated Tissue Factor ("tTF") (see, e.g. Kessler et al. (2005), Clin Cancer Res 11(17):6317, Tumor Necrosis Factor ("TNF") (see e.g., Mocellin at al. (2005). Cytokine Growth F R 16(1): 35), Scaffold Matrix Attachment Region binding protein 1 ("Smar1") derived p44 peptide (see, e.g., Jalota-Badhwar et al. (2007) J Biol Chem 282(13); 9902), interferon. TNF-Related Apoptosis-Inducing Ligand ("TRAIL") (see. e.g., Smyth et al. (2003). Cell Press 18: 1), Second-Mitochondria Activator of Caspases ("Smac") (see, e.g., Fandy et a. (2008), Mol Cancer 7:60). Von Hippel-Lindau tumor suppressor ("VHL") (see, e.g., Kodo et al, (2001) Exp Cell Res 264:117), procaspase, caspase, and IL-2, Toxins may include, without limitation, ricin, PAP, Diphtheria toxin, *Pseudomonas* exotoxin.

A "fusion protein" and a "fusion polypeptide" refer to a polypeptide having at least two portions covalently linked together, where each of the portions is a polypeptide having a different property. The property can be a biological property, such as activity in vitro or in vivo. The property can also be a simple chemical or physical property, such as binding to a target molecule, catalysis of a reaction, and the like. The portions can be linked directly by a single peptide bond or through a peptide linker containing one or more amino acid residues. Generally, the portions and the linker will be in reading frame with each other.

VI. Antibody or Antibody Fragment Active Agents

In a particular aspect of the invention, the therapeutic agent can be an antibody or antibody fragment which mediates one or more of complement activation, cell mediated cytotoxicity, apoptosis, necrotic cell death, and opsinization.

The term "antibody" herein is includes, without limitation, monoclonal antibodies, polyclonal antibodies, dimers, multimers, multispecific antibodies (e.g., bispecific antibodies). Antibodies can be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen can have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any class (e.g., IgG, IgE, IgM, IgD, and IgA) or subclass (e.g., IgG1, IgG2, IgG3, IgG4, IgA1 and IgA2) of immunoglobulin molecule. The immunoglobulins can be derived from any species.

"Antibody fragments" comprise a portion of a full length antibody, which maintain the desired biological activity. "Antibody fragments' are often the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments. However, other non-antigen-binding portions of antibodies can be "antibody fragments" as meant herein, e.g., without limitation, an antibody fragment can be a complete or partial Fc domain.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.gamma.RIII only, whereas monocytes express FcγRI, FcγRII and FcγRIII. To assess ADCC activity of a molecule of interest, an in vitro ADCC assay can be performed (U.S. Pat. No. 55,003,621; U.S. Pat. No. 5,821,337). Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. PNAS (USA), 95:652-656 (1998).

An antibody which "induces cell death" is one which causes a viable cell to become nonviable. Cell death in vitro can be determined in the absence of complement and immune effector cells to distinguish cell death induced by antibody-dependent cell-mediated cytotoxicity (ADCC) or complement dependent cytotoxicity (CDC). Thus, the assay for cell death can be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

VII. Method of Modulating the Distribution of Active Agents

Another aspect of the present invention takes advantage of the properties of the peptide ligand domain-containing conjugates disclosed herein to provide methods for modulating the distribution of an active agent within the tissue of an animal comprising administering to the animal a composition comprising a conjugate molecule which comprises a peptide ligand domain conjugated to an active agent, wherein the peptide ligand domain comprises a peptide of the SEQ ID NOs: 1 to-117 or homologs thereof, and wherein the administration of the composition to an animal results in a tissue distribution of the active agent which is different from the tissue distribution obtained upon administration of the active agent alone.

The compositions and methods of the present invention desirably provide for modulated tissue distribution of the active agent to a disease site. This desirably manifests itself in providing a concentration of the active agent at a disease site, and/or an increased or prolonged (half-life) blood level of the active agent, which is greater than that which would be provided if the active agent (in unconjugated form) was administered to the animal. This modulation may also manifest itself by enhancing the rate of tissue uptake of the conjugated peptide molecule, increasing the retention of the molecule at its target site, ie. at the tumor, enhancing the rate of diffusion of the conjugated peptide molecule in the tissue, and/or enhancing the distribution of the conjugated peptide molecule through the tissue, and matching the rate of tissue uptake of the conjugated peptide molecule to the rate of internalization of one or more tissue receptors. Such enhancements can be measured by any suitable method known in the art including, without limitation, the detection, localization and relative quantization of suitably labeled active agent, e.g., using radiographic, microscopic, chemical, immunologic or MRI techniques.

By "enhancing the rate" it is meant a rate that is that is at least about 33% greater, preferably at least about 25% greater, more preferably at least about 15% greater, most preferably at least about 10% greater. By a "greater concentration at a disease site" it is meant a concentration of the active agent in the conjugate at a disease site that is at least about 33% greater, preferably at least about 25% greater, more preferably at least about 15% greater, most preferably at least about 10% greater than the concentration of the unconjugated active agent at a comparable disease site.

Suitable disease sites include, without limitation, the sites of abnormal conditions of proliferation, tissue remodeling, hyperplasia, exaggerated wound healing in any bodily tissue including soft tissue, connective tissue, bone, solid organs, blood vessel and the like. More specific examples of such diseases include cancer, diabetic or other retinopathy, inflammation, fibrosis, arthritis, restenosis in blood vessels or artificial blood vessel grafts or intravascular devices and the like, cataract and macular degeneration, osteoporosis and other diseases of the bone, atherosclerosis and other diseases where calcification is frequently observed.

In a preferred aspect, the invention provides methods of diagnosing and/or treating a tumor, wherein the tumor is selected from the group consisting of oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia. In addition, the invention provides for method of predicting or determining a tumor's response to a chemotherapeutic agent, methods of treating a tumor, and kits for predicting the response of a mammalian tumor to a chemotherapeutic agent, wherein the tumor is a sarcoma, adenocarcinoma, squamous cell carcinoma, large cell carcinoma, small cell carcinoma, basal cell carcinoma, clear cell carcinoma, oncytoma or combinations thereof.

In another aspect, the invention provides compositions and methods of use of said compositions, wherein administering the composition to an animal results in a blood level of the active agent which is greater than the blood level obtained upon administration of the active agent alone. Any suitable measure of the active agent's blood level can be used, including without limitation, $C_{max}$, $C_{min}$, and AUC. By "greater than the blood level obtained upon administration of the active agent alone" it is meant a blood level that is at least about 33% greater, preferably at least about 25% greater, more preferably at least about 15% greater, most preferably at least about 10% greater.

In yet another aspect, the invention provides compositions and methods of use of said compositions, wherein the administration of the composition to an animal results in a blood level half-life of the active agent which is greater than the blood level half-life obtained upon administration of the active agent alone. By "greater than the blood half-life obtained upon administration of the active agent alone" it is meant a half-life that is at least about 33% greater, preferably at least about 25% greater, more preferably at least about 15% greater, most preferably at least about 10% greater.

VIII. Formulations and Administration

For use in vivo, the active agent coupled a peptide ligand domain, such as the SEQ ID NOs: 1-117 and homologs thereof, is desirably is formulated into a pharmaceutical composition comprising a physiologically acceptable carrier. Any suitable physiologically acceptable carrier can be used within the context of the invention, depending on the route of administration. Those skilled in the art will appreciate those carriers that can be used in to provide a pharmaceutical composition suitable for the desired method of administration.

The administration of the pharmaceutical compositions of the present invention can be accomplished via any suitable route including, but not limited to, intravenous, subcutaneous, intramuscular, intraperitoneal, intratumoral, oral, rectal, vaginal, intravesical, and inhalational administration, with intravenous and intratumoral administration being most preferred. The composition can further comprise any other suitable components, especially for enhancing the stability of the composition and/or its end use. Accordingly, there is a wide variety of suitable formulations of the composition of the invention. The following formulations and methods are merely exemplary and are in no way limiting.

The pharmaceutical compositions can also include, if desired, additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

The carrier typically will be liquid, but also can be solid, or a combination of liquid and solid components. The carrier desirably is physiologically acceptable (e.g., a pharmaceutically or pharmacologically acceptable) carrier (e.g., excipient or diluent). Physiologically acceptable carriers are well known and are readily available. The choice of carrier will be determined, at least in part, by the location of the target tissue and/or cells, and the particular method used to administer the composition.

Typically, such compositions can be prepared as injectables, either as liquid solutions or suspensions; solid forms suitable for using to prepare solutions or suspensions upon the addition of a liquid prior to injection can also be prepared; and the preparations can also be emulsified. The pharmaceutical formulations suitable for injectable use include sterile aqueous solutions or dispersions; formulations containing known protein stabilizers and lyoprotectants, formulations including sesame oil, peanut oil or aqueous propylene glycol, and sterile powders for the extemporaneous preparation of sterile injectable solutions or dispersions. In all cases the formulation must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxycellulose. Dispersions can also be prepared in glycerol, liquid polyethylene glycols, and mixtures thereof and in oils. Under ordinary conditions of storage and use, these preparations contain a preservative to prevent the growth of microorganisms.

The peptide ligand domain-containing conjugate, such as can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The formulations can be presented in unit dose or multi dose sealed containers, such as ampules and vials, and can be stored in a freeze dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. In a preferred embodiment of the invention, the peptide ligand domain-containing conjugate is formulated for injection (e.g., parenteral administration). In this regard, the formulation desirably is suitable for intratumoral administration, but also can be formulated for intravenous injection, intraperitoneal injection, subcutaneous injection, and the like.

The invention also provides, if desirable, embodiments in which the peptide ligand domain-containing conjugate (i.e., the peptide ligand domain-containing polypeptide conjugated to an active agent) is further conjugated to polyethylene glycol (PEG). PEG conjugation can increase the circulating half-life of these polypeptides, reduce the polypeptide's immunogenicity and antigenicity, and improve their bioactivity. If used, any suitable method of PEG conjugation can be used, including but not limited to, reacting methoxy-PEG with a peptide's available amino group(s) or other reactive sites such as, e.g., histidines or cysteines. In addition, recombinant DNA approaches can be used to add amino acids with PEG-reactive groups to the peptide ligand domain-containing conjugate. Further, releasable and hybrid PEG-ylation strategies can be used in accordance with the aspects of the present invention, such as the PEG-ylation of polypeptide, wherein the PEG molecules added to certain sites in the peptide ligand domain-containing conjugatemolecule are released in vivo. Examples of PEG conjugation methods are known in the art. See, e.g., Greenwald et al., Adv. Drug Delivery Rev. 55:217-250 (2003).

Formulations suitable for administration via inhalation include aerosol formulations. The aerosol formulations can be placed into pressurized acceptable propellants, such as dichlorodifluoromethane, propane, nitrogen, and the like. They also can be formulated as non pressurized preparations, for delivery from a nebulizer or an atomizer.

Formulations suitable for anal administration can be prepared as suppositories by mixing the active ingredient with a variety of bases such as emulsifying bases or water soluble bases. Formulations suitable for vaginal administration can be presented as pessaries, tampons, creams, gels, pastes, foams, or spray formulas containing, in addition to the active ingredient, such carriers as are known in the art to be appropriate.

In addition, the composition of the invention can comprise additional therapeutic or biologically active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

In the case of inhalational therapy, the pharmaceutical composition of the present invention is desirably in the form of an aerosol. Aerosol and spray generators for administering the agent if in solid form are available. These generators provide particles that are respirable or inhalable, and generate a volume of aerosol containing a predetermined metered dose of a medicament at a rate suitable for human administration. Examples of such aerosol and spray generators include metered dose inhalers and insufflators known in the art. If in liquid form, the pharmaceutical compositions of the invention can be aerosolized by any suitable device.

When used in connection with intravenous, intraperitoneal or intratumoral administration, the pharmaceutical composition of the invention can comprise sterile aqueous and non-aqueous injection solutions, suspensions or emulsions of the active compound, which preparations are preferably isotonic with the blood of the intended recipient. These preparations can contain one or more of anti-oxidants, buffers, surfactants, cosolvents, bacteriostats, solutes which render the compositions isotonic with the blood of the intended recipient, and other formulation components known in the art. Aqueous and non-aqueous sterile suspensions can include suspending agents and thickening agents. The compositions can be presented in unit-dose or multi-dose containers, for example sealed ampoules and vials.

The methods of the present invention can also be part of combination therapy. The phrase "combination therapy" refers to administering a therapeutic agent in accordance with the invention together with another therapeutic composition in a sequential or concurrent manner such that the beneficial effects of this combination are realized in the mammal undergoing therapy.

XI. The Invention is Applicable to Many Conditions

The compositions and methods of the invention are suitable for use in diagnosing or treating various diseases including, but not limited to, wherein the disease site is, abnormal conditions of proliferation, tissue remodeling, hyperplasia, exaggerated wound healing in any bodily tissue including soft tissue, connective tissue, bone, solid organs, blood vessel and the like. More specific examples of such diseases include cancer, diabetic or other retinopathy, inflammation, fibrosis, arthritis, restenosis in blood vessels or artificial blood vessel grafts or intravascular devices and the like, cataract and macular degeneration, osteoporosis and other diseases of the bone, atherosclerosis and other diseases where calcification is frequently observed.

In a preferred aspect, the invention provides methods of diagnosing and/or treating a tumor, wherein the tumor is selected from the group consisting of oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia. In addition, the invention provides for method of predicting or determining a tumor's response to a chemotherapeutic agent, methods of treating a tumor, and kits for predicting the response of a mammalian tumor to a chemotherapeutic agent, wherein the tumor is a sarcoma, adenocarcinoma, squamous cell carcinoma, large cell carcinoma, small cell carcinoma, basal cell carcinoma, clear cell carcinoma, oncytoma or combinations thereof.

The invention provides for embodiments wherein the disease is in a mammal, including but not limited to, a human.

X. Kits

The invention provides kits for the treatment of tumors comprising a pharmaceutical formulation and instructions for use of the formulation in the treatment of tumors, wherein the pharmaceutical formulation comprises a conjugate molecule which comprises a peptide ligand domain conjugated to an active agent, and wherein the peptide ligand domain comprises a peptide of the SEQ ID NOs: 1-137, 139 or 140, or 141-143, or a homolog thereof, wherein the peptide ligand domain has an affinity for human serum albumin characterized by an equilibrium dissociation constant (Kd) of about 700 μM or less, and, optionally, wherein the conjugate molecule further comprises a second peptide ligand domain, and instructions for use of said kits (e.g., FDA approved package inserts).

XI. Affinity Purification

Affinity chromatography (also called affinity purification) makes use of specific binding interactions between molecules. A particular ligand is chemically immobilized or "coupled" to a solid support so that when a complex mixture is passed over the column, those molecules having specific binding affinity to the ligand become bound. After other sample components are washed away, the bound molecule is stripped from the support, resulting in its purification from the original sample.

Each specific affinity system requires its own set of conditions and presents its own peculiar challenges for a given research purpose. Other Protein Methods articles describe the factors and conditions associated with particular purification systems (see links in side bar near the end of this page). Nevertheless, the general principles involved are the same for all ligand-target binding systems, and these concepts are the focus of this overview.

Affinity purification generally involves the following steps:

(1) Incubate crude sample with the affinity support to allow the target molecule in the sample to bind to the immobilized ligand.

(2) Wash away nonbound sample components from the support.

(3) Elute (dissociate and recover) the target molecule from the immobilized ligand by altering the buffer conditions so that the binding interaction no longer occurs.

A single pass of a serum or cell-lysate sample through an affinity column can achieve greater than 1,000-fold purification of a specific protein so that only a single band is detected after gel electrophoresis (e.g., SDS-PAGE) analysis.

Ligands that bind to general classes of proteins (e.g., antibodies) or commonly used fusion protein tags (e.g., 6×His) are commercially available in pre-immobilized forms ready to use for affinity purification. Alternatively, more specialized ligands such as specific antibodies or antigens of interest can be immobilized using one of several commercially available activated affinity supports; for example, a peptide antigen can be immobilized to a support and used to purify antibodies that recognize the peptide.

Most commonly, ligands are immobilized or "coupled" directly to solid support material by formation of covalent chemical bonds between particular functional groups on the ligand (e.g., primary amines, sulfhydryls, carboxylic acids, aldehydes) and reactive groups on the support (see related article on Covalent Immobilization). However, indirect coupling approaches are also possible. For example, a GST-tagged fusion protein can be first captured to a glutathione support via the glutathione-GST affinity interaction and then secondarily chemically crosslinked to immobilize it. The immobilized GST-tagged fusion protein can then be used to affinity purify binding partner(s) of the fusion protein.

Most affinity purification procedures involving protein:ligand interactions use binding buffers at physiologic pH and ionic strength, such as phosphate buffered saline (PBS). This is especially true when antibody:antigen or native protein:protein interactions are the basis for the affinity purification. Once the binding interaction occurs, the support is washed with additional buffer to remove nonbound components of the sample. Nonspecific (e.g., simple ionic) binding interactions can be minimized by adding low levels of detergent or by moderate adjustments to salt concentration in the binding and/or wash buffer. Finally, elution buffer is added to break the binding interaction and release the target molecule, which is then collected in its purified form. Elution buffer can dissociate binding partners by extremes of pH (low or high), high salt (ionic strength), the use of detergents or chaotropic agents that denature one or both of the molecules, removal of a binding factor or competition with a counter ligand. In most cases, subsequent dialysis or desalting is required to exchange the purified protein from elution buffer into a more suitable buffer for storage or downstream analysis.

The most widely used elution buffer for affinity purification of proteins is 0.1M glycine.HCl, pH 2.5-3.0. This buffer effectively dissociates most protein:protein and antibody:antigen binding interactions without permanently affecting protein structure. However, some antibodies and proteins are damaged by low pH, so eluted protein fractions should be neutralized immediately by addition of 1/10th volume of alkaline buffer such as 1M Tris.HCl, pH 8.5. Other elution buffers for affinity purification of proteins include:

Affinity purification involves the separation of molecules in solution (mobile phase) based on differences in binding interaction with a ligand that is immobilized to a stationary material (solid phase). A support or matrix in affinity purification is any material to which a biospecific ligand is covalently attached. Typically, the material to be used as an affinity matrix is insoluble in the system in which the target molecule is found. Usually, but not always, the insoluble matrix is a solid. Hundreds of substances have been described and utilized as affinity matrices.

| Common elution buffers systems for protein affinity purification. | |
|---|---|
| Condition | Buffer |
| pH | 100 mM glycine•HCl, pH 2.5-3.0 |
| | 100 mM citric acid, pH 3.0 |
| | 50-100 mM triethylamine or triethanolamine, pH 11.5 |
| | 150 mM ammonium hydroxide, pH 10.5 |
| Ionic strength and/or chaotropic effects | 3.5-4.0M magnesium chloride, pH 7.0 in 10 mM Tris |
| | 5M lithium chloride in 10 mM phosphate buffer, pH 7.2 |
| | 2.5M sodium iodide, pH 7.5 |
| | 0.2-3.0 sodium thiocyanate |
| Denaturing | 2-6M guanidine•HCl |
| | 2-8M urea |
| | 1% deoxycholate |
| | 1% SDS |
| Organic | 10% dioxane |
| | 50% ethylene glycol, pH 8-11.5 (also chaotropic) |
| Competitor | >0.1M counter ligand or analog |

Useful affinity supports are those with a high surface-area to volume ratio, chemical groups that are easily modified for covalent attachment of ligands, minimal nonspecific binding properties, good flow characteristics and mechanical and chemical stability. When choosing an affinity support or matrix for any separation, perhaps the most important question to answer is whether a reliable commercial source exists for the desired matrix material in the quantities required.

Immobilized ligands or activated affinity support chemistries are available for use in several different formats. Most commonly, crosslinked beaded agarose or polyacrylamide resins are used for column- or small-scale purification procedures. Magnetic particles to which affinity ligands have been immobilized are especially useful for cell separations and certain automated purification procedures. Even polystyrene microplates, more commonly used for assay purposes, can be used as the support for immobilizing ligands to purify binding partners.

Porous gel supports generally provide the most useful properties for affinity purification of proteins. These types of supports are usually sugar- or acrylamide-based polymer resins that are produced in solution (i.e., hydrated) as 50-150 µm diameter beads. The beaded format allows these resins to be supplied as wet slurries that can be easily dispensed to fill and "pack" columns with resin beds of any size. The beads are extremely porous and large enough that biomolecules (proteins, etc.) can flow as freely into and through the beads as they can between and around the surface of the beads. Ligands are covalently attached to the bead polymer (external and internal surfaces) by various means. The result is a loose matrix in which sample molecules can freely flow past a high surface area of immobilized ligand By far the most widely used matrix for protein affinity purification techniques is crosslinked beaded agarose, which is typically available in 4% and 6% densities. (This means that a 1 ml resin-bed is more than 90% water by volume.)

Several methods of antibody purification involve affinity purification techniques. Typical laboratory-scale antibody production involves relatively small volumes of serum, ascites fluid or culture supernatant. Depending on how the antibody will be used for various assay and detection methods, it must be partially or fully purified. Three levels of purification specificity include the following approaches:

Precipitation with ammonium sulfate. This simple technique provides crude purification of total immunoglobulin from other serum proteins.

Affinity purification with immobilized Protein A, G, A/G or L. These proteins bind to most species and subclasses of IgG, the most abundant type of immunoglobulin produced by mammals in response to immunogens. Ready-to-use resins and purification kits with these proteins are available in many package sizes and formats.

Affinity purification with immobilized antigen. Covalently immobilizing purified antigen (i.e., the peptide or hapten used as the immunogen to induce production of antibody by the host animal) to an affinity support allows the specific antibody to be purified from crude samples. Activated resins and complete kits for preparing immobilized antigens via a variety of chemistries are available. See also: Seo et al., Characterization of a *Bifidobacterium longum* BORI dipeptidase belonging to the U34 family, Appl Environ Microbiol. 2007 September; 73(17):5598-606; Clonis Y D, Affinity chromatography matures as bioinformatic and combinatorial tools develop, J Chromatogr A. 2006 Jan. 6; 1101(1-2):1-24; Jmeian Y & El Rassi Z, Liquid-phase-based separation systems for depletion, prefractionation and enrichment of proteins in biological fluids for in-depth proteomics analysis, Electrophoresis. 2009 January; 30(1): 249-61.

The invention provides scFvs which are at least 80%, preferably at least 85%, more preferably at least 90%, even more preferably at least 95%, most preferably at least 99% identical to any one of SEQ ID NOs: 113-116 and have a KD for SPARC protein of at least $4 \times 10^{-7}$ M, preferably $4 \times 10^{-6}$ M, more preferably $7 \times 10^{-5}$ M or a KD for SPARC protein from about $3.3 \times 10^{-7}$ to about $7.8 \times 10^{-5}$. In addition, the invention provides for scFvs which are at least 80%, preferably at least 85%, more preferably at least 90%, even more preferably at least 95%, most preferably at least 99% identical to any one of SEQ ID NOs: 113-116; which are at least 80%, preferably at least 85%, more preferably at least 90%, even more preferably at least 95%, most preferably at least 99% identical to any one of the CDRs in SEQ ID NOs: 113-116 and which have a KD for SPARC protein of at least $4 \times 10^{-7}$ M, preferably $4 \times 10^{-6}$ M, more preferably $7 \times 10^{-5}$ M or a KD for SPARC protein from about $3.3 \times 10^{-7}$ M to about $7.8 \times 10^{-5}$ M.

The following examples further illustrate the invention but, of course, should not be construed as in any way limiting its scope.

Example 1

This Example demonstrates the identification of SPARC binding peptides using the phage display technology and the incorporation of such SPARC binding peptides into molecules for tumor therapy.

Figure 1:
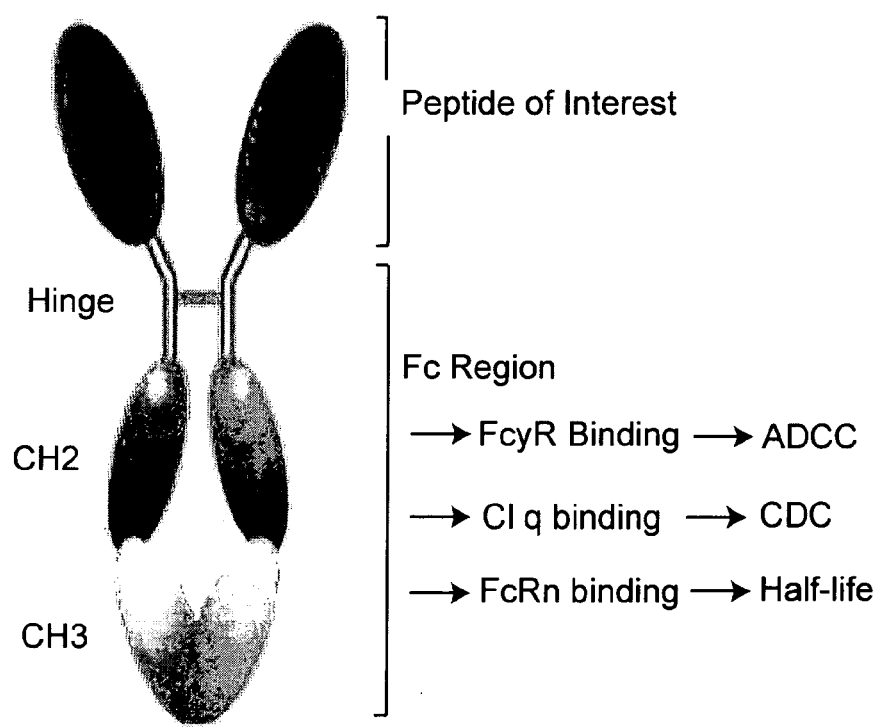
FIG. 1 depicts the general concept of fusing a binding peptide to a therapeutic or diagnostic agent. In the example depicted in this drawing, the therapeutic agent is an antibody Fc domain.

Specifically, a major goal was to generate a molecule with a SPARC binding peptide conjugated to a therapeutic or diagnostic agent. In particular, the goal was to generate a SPARC binding peptide-Fc fusion protein (FIG. 1), where the antibody Fc domain acts as a therapeutic agent by stimulating immune functions such as, e.g., antibody dependent cytotoxicity (ADC) or cell dependent cytotoxicity (CDC).

Figure 2:
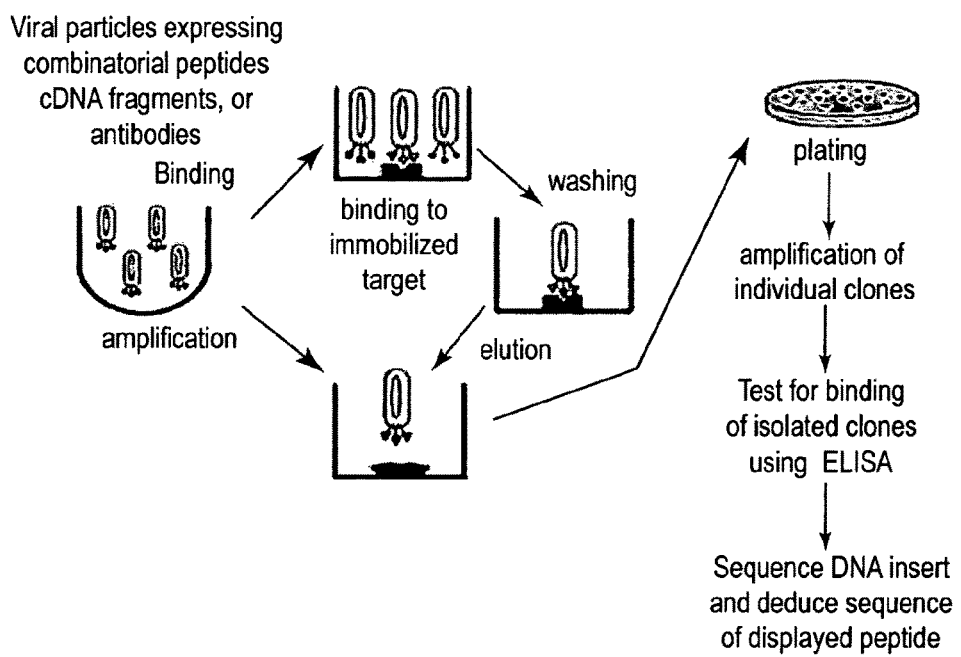
FIG. 2 depicts the general strategy for the iterative screening of a phage display library.

The general principle of display methodologies is to link a ligand (peptide, protein) to the gene coding for this ligand (see FIG. 2). In the phage display technique, this is obtained by fusing the ligand gene to the gene coding for a coat protein of a filamentous phage. The recombinant phage genome is then introduced into *Escherichia coli* where the hybrid protein will be expressed together with all the other phage proteins. The fusion protein will then be incorporated into the phage coat containing the phage genome (containing the ligand gene). The secreted phage particle displaying the ligand can be selected on an immobilized target while all the non-binding phages are washed away. After an elution step, the recovered phage is used to infect *E. coli* to allow the amplification of this phage for a new round of selection and eventually for the binding analysis.

Accordingly, a commercial peptide phage display library (12-mer peptides in M13) was screened for peptides which bind to SPARC. The target, SPARC is an acidic glycoprotein with a PI of 4.6. By immobilization on 96-wells plates with pH 9.6 coating buffer, Ph.D.-12 peptide library was screened four rounds to select peptide binders using phage display technology. Specifically, bound phages were eluted with an acidic eluting solution in the 1st round of screening. Then the screening stringency was enhanced gradually by decreasing the target protein concentration and increasing the percentage of Tween-20 in washing buffer. At the same time, competitive elution with excess target was adopted to improve the screening specificity. Finally, after four rounds of screening, ssDNA of selected clones were subjected to DNA sequencing. At the same time, the binding of the positive phages to the target protein was validated using phage ELISA.

The results of this screening of a peptide phage display library for SPARC binding peptides are shown in FIGS. 3 & 4. SPARC binding can be quantified by the number of phage clones isolated which encode peptides with the same sequence (FIG. 3) or the avidity of SPARC binding as measured by the binding of peptide-expressing phage to SPARC-coated microtiter plate wells (FIG. 4). Two of the peptides identified by phage display, PD 15 (SEQ ID NO: 1) and PD 21 (SEQ ID NO: 2) were further characterized.

Figure 5:
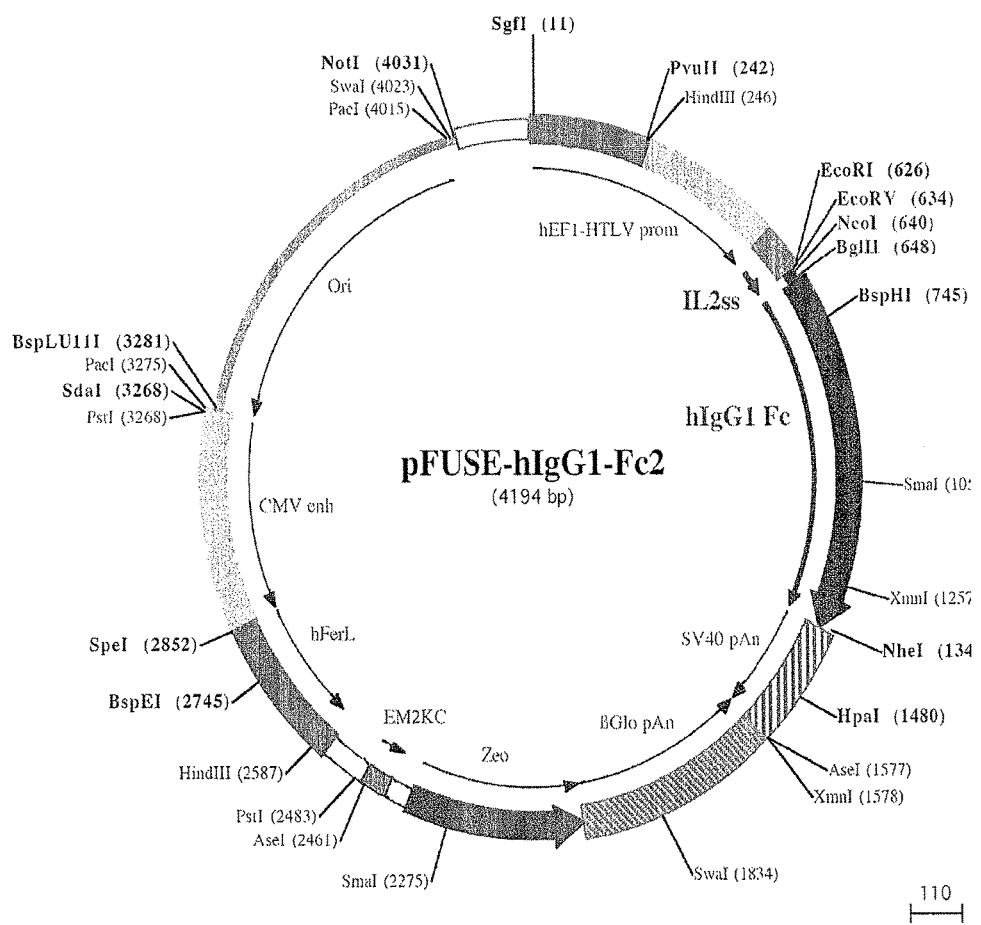
FIG. 5 depicts the cloning of either peptide peptides PD 15 or PD21 into the pFUSE-hIgG1-Fc2 vector to give PD15 or PD21 Fc fusion protein.

PD 15 and PD 21 were then cloned into the expression vector pFUSE-hIg1-Fc2 (FIG. 5), resulting in plasmids that encode PD 15-Fc and PD 21-Fc fusion proteins (FIG. 6). These fusion proteins were expressed and successfully purified as demonstrated by polyacrylamide gel electrophoresis (FIG. 7).

Protein microarray analysis (see, FIG. 8) of PD 15 and PD 21 showed only minimal cross reactivity with the non-SPARC proteins in 5,000 proteins on the array assayed (Invitrogen, ProtoArray v.3).

Concentration dependent binding ELISA assays demonstrated PD 15 and PD 21 binding to SPARC was shown to be only slightly weaker than that of an anti-SPARC antibody (FIG. 9). The SPARC binding Kd of PD 15 is $4.1 \pm 0.6 \times 10^{-8}$ M and that of PD 21 is $1.0 \pm 0.7 \times 10^{-7}$ M. (The anti-SPARC antibody tested has a SPARC binding Kd of $6.2 \pm 3.4 \times 10^{-9}$ M, i.e., the antibody binds SPARC only slightly more avidly.)

FIGS. 10 and 11 show the co-localization of SPARC (as indicated by immunohistochemical (IHC) staining with an anti-SPARC antibody) and the binding of PD 15 and PD 21 in sections of a human brain tumor (which have been epitope tagged for IHC staining.). As shown in FIG. 10, the literature report of stabilin 1 binding to SPARC was not verified, as stab-Fc did not bind to tumor tissue whereas PD15 and PD21 did (FIG. 11).

Sequence homology analysis of the SPARC-binding peptides isolated by phage display demonstrated that a number of the SPARC-binding peptide sequences isolated had sequence identities with a region of the Elastin shown in FIG. 12.

Thus, this Example demonstrates SPARC binding peptides can be identified by phage display and how to further characterize the identified peptides. Of the two clones worked up, PD 15 and PD 21, PD 15 exhibited a higher affinity for SPARC than PD 21 in ELSIA and IHC experiments.

Example 2

The PD 15 and PD 21-Fc fusion proteins were assayed for antitumor activity in a murine-human PC3 prostatecarcinoma xenograft model. Both PD 15 and PD 21-Fc fusion proteins demonstrated statistically significant tumor growth inhibition (FIG. 13). PD15 exhibited better antitumor activity than PD21 against the PC3 xenograft. In a mouse-human HT29 colon xenograft model-PD21 exhibited better antitumor activity than PD15, with activity closely equivalent to Abraxane (FIG. 14).

Example 3

This Example demonstrates the potential immunogenicity of the SPARC-binding peptides.

ProPred is a graphical web tool for predicting MHC class II binding regions in antigenic protein sequences (see Singh et al.: ProPred: prediction of HLA-DR binding sites. Bioinformatics 2001, 17(12):1236-7). The server implement matrix based prediction algorithm, employing amino-acid/position coefficient table deduced from literature. The predicted binders can be visualized either as peaks in graphical interface or as colored residues in HTML interface. This server might be a useful tool in locating the promiscuous binding regions that can bind to several HLA-DR alleles.

The results of a ProPred analysis of SPARC-binding peptides identified with phage display, including PD 21 and PD 15 indicate that only a few HLA-DR molecules will present these peptides and suggest that the peptides will not be very immunogenic.

Any peptide disclosed herein, including, e.g., SEQ ID: 1-112 or 117, showing high affinity can be similarly analyzed for low or no immunogenicity.

Example 4

Antibody fragments also can be displayed on phages using different formats. Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. The most common formats for antibody phage display include the use of scFv libraries. Large collections of antibody variants can thus be screened for the presence of an antigen-binding clone.

The overall strategy was to first, screen a human antibody phage display libraries by ELISA with SPARC as antigen.

At the start, HuScL-3® was screened four rounds (three rounds with acidic elution and one round with competitive elution) and 17 positive clones were selected by phage ELISA. DNA sequencing of these clones revealed two unique antibody sequences, between which the 1st sequence was shared by 15 positive clones and the 2nd one was shared by remaining two positive clones. After that, the binding specificity of the two unique antibodies was validated by soluble scFv ELISA.

Next, HuScL-2® was screened for three rounds (two rounds with trypsin-digestion elution and one round with competitive elution). In the end, 30 positive clones were selected by phage ELISA. According to the sequencing results, 29 clones shared one antibody sequence and the remaining one clone encoded another unique antibody. After that, the binding specificity of these two antibodies was validated by soluble scFv ELISA as well.

Four unique ScFv against SPARC were identified, ScFv 3-1, ScFv 3-2, ScFv 2-1, and ScFv 2-2 (SEQ ID NOs: 113-116). FIG. 17 shows the sequences of ScFv 3-1, ScFv 3-2, ScFv 2-1, and ScFv 2-2 (SEQ ID NOs: 113-116) with the antigen binding CDRs underlined.

Example 5

This Example discloses the purification of exemplary SPARC binding ScFv s.

FIG. 18 shows the Nickle column purification and characterization of ScFv2.1 by terminal amino acid sequencing and SDS-PAGE of bacterial isolated scfv2.1 (A, the expressed sequence; B, affinity chromatography; C, SDS PAGE; D, N-terminal amino acid sequence data.

FIG. 19 shows the purification and characterization of scFv2.1 by terminal amino acid sequencing and SDS-PAGE of bacterial isolated Scfv3.1 (A, the expressed sequence; B, affinity chromatography; C, SDS PAGE; D, N-terminal amino acid sequence data.

FIG. 20 shows the determination of the KD of purified ScFv2.1, scFv3.1 and scFv3.2 for binding SPARC. A, Sensorgrams of typical Biacore™ surface plasmon resonance experiment using SPARC immobilized chip and ScFv2.1 as flow through; B, KDs of ScFv2-1, ScFV3-1, and ScFV3-2 against (HTI SPARC is platelet SPARC obtained from HTI; Abx SPARC is SPARC purified at Abraxis from engineered HEK293 cells).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating cancer differentially expressing SPARC in a mammalian subject comprising:
(a) preparing a composition comprising one or more SPARC binding ScFvs whose amino acid sequences consist of SEQ ID NOS: 113-116, wherein each of the one or more ScFvs specifically binds SPARC and is conjugated to:
i) a cytotoxic moiety that is effective to inhibit the proliferation and/or survival of cancer cells in the mammalian subject, or
ii) an antibody fragment comprising a functional antibody Fc domain capable of mediating antibody-dependent cell-mediated cytotoxicity (ADCC) or complement dependent cytotoxicity (CDC), and
wherein the composition, optionally, further comprises a pharmaceutically acceptable carrier; and
(b) administering to a mammalian subject a therapeutically effective amount of the composition.

2. The method of claim 1, wherein the functional antibody Fc domain comprises SEQ ID NO: 118.

3. The method of claim 1, wherein the cytotoxic moiety is selected from the group consisting of a radionuclide, adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosourea, paclitaxel, pamidronate, pentostatin, plicamycin, procarbazine, rituximab, streptozocin, teniposide, thioguanine, thiotepa, taxanes, vinblastine, vincristine, vinorelbine, combretastatins, discodermolides, transplatinum, 5-fluorouracil, genistein, Truncated Tissue Factor ("tTF"), Tumor Necrosis Factor ("TNF"), Scaffold Matrix Attachment Region binding protein 1 ("Smar1") derived p44 peptide, interferon, TNF-Related Apoptosis-Inducing Ligand ("TRAIL"), Second-Mitochondria Activator of Caspases ("Smac"), Von Hipel-Lindau tumor suppressor ("VHL") procaspase, caspase, IL-2, a non-Fc domain antibody fragment, and combinations thereof.

4. The method of claim 1, wherein the mammalian subject is a human.

* * * * *